L

US012214053B2

(12) United States Patent
Ferreira

(10) Patent No.: US 12,214,053 B2
(45) Date of Patent: *Feb. 4, 2025

(54) METHODS OF IMPROVING ADENO-ASSOCIATED VIRAL TRANSDUCTION

(71) Applicant: uniQure IP B.V., Amsterdam (NL)

(72) Inventor: Valerie Ferreira, Amsterdam (NL)

(73) Assignee: uniQure IP B.V., Amsterdam (NL)

( * ) Notice: Subject to any disclaimer, the term of this patent is extended or adjusted under 35 U.S.C. 154(b) by 350 days.

This patent is subject to a terminal disclaimer.

(21) Appl. No.: 16/896,811

(22) Filed: Jun. 9, 2020

(65) Prior Publication Data

US 2020/0360535 A1 Nov. 19, 2020

Related U.S. Application Data

(63) Continuation of application No. PCT/EP2018/086487, filed on Dec. 21, 2018.

(30) Foreign Application Priority Data

Dec. 22, 2017 (EP) .................................... 17210487

(51) Int. Cl.
C12N 15/86 (2006.01)
A61K 48/00 (2006.01)
(52) U.S. Cl.
CPC .......... A61K 48/0016 (2013.01); C12N 15/86 (2013.01)
(58) Field of Classification Search
CPC ..................................................... C12N 15/86
See application file for complete search history.

(56) References Cited

PUBLICATIONS

Jacobs et al, The Liver as a Target Organ for Gene Therapy: State of the Art, Challenges, and Future Perspectives, 2012, Pharmaceuticals, 5: 1372-1392 (Year: 2012).*
Mansouri et al , Atheroprotective Effect of Human Apolipoprotein A5 in a Mouse Model of Mixed Dyslipidemia, Circulation Research , 2008, vol. 103, No. 5: 450-453 (Year: 2008).*
Murphy et al , Gene therapy for haemophilia, British Journal of Haematology, 2008, vol. 140, issue 5: 477-594 (Year: 2008).*
Al Kuzmin, MJ Finegold and RC Eisensmith: "Macrophage depletion increases the safety, efficacy a. nd .p ersistence of adenovirus-mediated gene transfer in vivo" Departments of Cell Biology and Pathology, Baylor College of Medicine, Houston, TX, USA, Gene Therapy (1997) 4, 309-316, 1997.
Allen et al: "Toxicity of drug carriers to the mononuclear phagocyte system", Advanced Drug Delivery Reviews, Elsevier, Amsterdam. NL,vol. 2, No. 1, Oct. 1, 1988 (Oct. 1, 1988)• pp. 55-67, XP023844321,ISSN: 0169-409X, DOI: 10.1016/0169-409X(88)90005-1, [retrieved on Oct. 1, 1988] abstract, p. 56, p. 61.
Frank Jacobs et al: "The Liver as a Target Organ for Gene Therapy: State of the Art, Challenges, and Future Perspectives", Pharmaceuticals, vol. 5, No. 12, Dec. 10, 2012 (Dec. 10, 2012), pp. 1372-1392, XP055469452, CH ISSN: 1424-8247, DOI: 10.3390/ph5121372 abstract p. 1374, paragraph 2 p. 138-p. 1; figures 1,2; table 1.
Gerhard Wolff et al.: "Enhancement of In Vivo Adenovirus-Mediated Gene Transfer and Expression by Prior Depletion of Tissue Macrophages in the Target Organ", Journal of Virology, Jan. 1997, p. 624-629 0022-538X/97/$04.00 0 Copyright ? 1997, American Society for Microbiology vol. 71, No. 1.
Gilles Mou Lay et al: "Polymers for Improving the In Vivo Transduction Efficiency of AAV2 Vectors",PLOS ONE, vol. 5, No. 12,Dec. 28, 2010 (Dec. 28, 2010), p. e15576, XP055554758, DOI: 10.1371/journal.pone.0015576 abstract p. 6-p. 7, figures 1-6.
Gudrun Schiedner et al.: "Selective Depletion or Blockade of Kupffer Cells Leads to Enhanced and Prolonged Hepatic Transgene Expression Using High-Capacity Adenoviral Vectors", Center for Molecular Medicine and Institute for Pathology, University of Cologne, D-50931 Cologne, Germany Department of Cell Biology & Immunology, Vrije Universiteit Amsterdam, Amsterdam, The Netherlands 1081, Department of Gene Therapy, University of Ulm, D-89081 Ulm, Germany, Molecular Therapy vol. 7, No. 1, Jan. 2003.
Kwikker's Karin L et al: "Lipid Nanoparticle Pre-Treatment Improves rAAV Diffusion in the Primate Liver and Enables an Increase of Therapeutic Transgene Expression", Molecular Therapy the Journal of the American Society of Gene Therapy, Academic Press; Nature Publishing Group, US,vol. 26, No. 5, Suppl. 1, Apr. 30, 2018 (Apr. 30, 2018), p. 249, XP009511152,ISSN: 1525-0016.
Lisa M. Kattenhorn et al: "Adeno-Associated Virus Gene Therapy for Liver Disease", Human Gene Therapy, vol. 27, No. 12,Dec. 1, 2016 (Dec. 1, 2016), pp. 947-961, XP055447652, & Conference on Changing the Face of Modern Medicine—Stem Cells and Gene Therapy; Florence, Italy; Oct. 18-21, 2016 ISSN: 1043-0342, DOI: 0.1089/hum.2016.160 Abstract p. 957, col. 1, paragraph 2-p. 958; table 1.
Matthew L Hillestad et al: "658. Enhancing Systemic Delivery of Recombinant Adena-Associated Viruses Through Kupffer Cell Depletion" , Molecular Therapy, May 1, 2011 (May 1, 2011), page S253,XP055469832, DOI: 10.1016/S1525-0016(16)37231-8, Retrieved from the Internet: URL:http://www.cell.com/molecular-therapyfamily/molecular-therapy/pdf/S1525-0016(16 )37231-8.pdf.
Sangeetha Hareendran et al: "Adena-associated virus (AAV) vectors in gene therapy: immune challenges and strategies to circumvent them: Immune challenges to AAV vectors", Reviews in Medical Virology, vol. 23, No. 6,Nov. 1, 2013 (Nov. 1, 2013), pp. 399-413, XP055377725, GB ISSN: 1052-9276, DOI: 10.1002/rmv.1762, figures 1-6; table 1.
Shen Shen et al: "Functional Analysis of the Putative Integrin Recognition Motif on Adena-associated Virus 9", Journal of Biological Chemistry, vol. 290. No. 3. Jan. 16, 2015 (Jan. 16, 2015), pp. 1496-1504, XP055469551, US ISSN: 0021-9258, DOI:10.1074/jbc. M114.608281, abstract.
Snoeys et al: "Lipid Emulsions Potently Increase Transgene Expression in Hepatocytes after Adenoviral Transfer", Molecular Therapy : The Journal of the American Society of Gene Therapy, Academic Press; Nature Publishing Group, US, vol. 13, No. 1,Jan. 1, 2006 (Jan. 1, 2006), pp. 98-107,XP005197698, ISSN: 1525-0016, OI:10.1016/J.YMTHE.2005.06.477 cited in the application abstract, p. 99, col. 1-col. 2, paragraph p. 105, col. 1, paragraph 2.

(Continued)

Primary Examiner — Ekaterina Poliakova-Georgantas
(74) Attorney, Agent, or Firm — N.V. Nederlandsch Octrooibureau

(57) ABSTRACT

Described herein are saturating agents, AAV gene therapy vectors, and therapeutic agents, as well as methods and kits comprising the same.

8 Claims, 7 Drawing Sheets
(2 of 7 Drawing Sheet(s) Filed in Color)

(56) References Cited

PUBLICATIONS

International Search Report mailed Feb. 27, 2019 in corresponding International Application No. PCT/EP2018/086487, 5 pages.
Pillay et al. (2017) "Host determinants of adeno-associated viral vector entry" Curr Opin Virol., 24, 124-131.
Stasiak et al. (2019) "Human adenovirus binding to host cell receptors: a structural view" Medical Microbiology and Immunology, 209, 325-333.

* cited by examiner

FIG. 3A
FIG. 3B
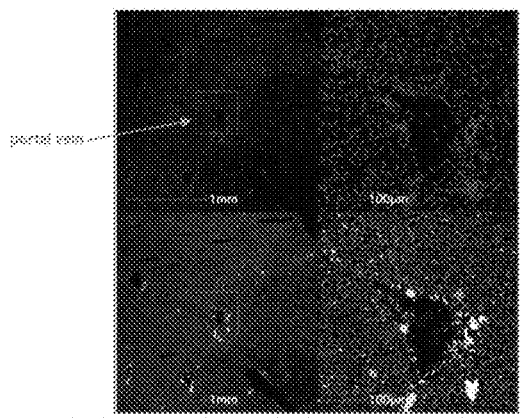
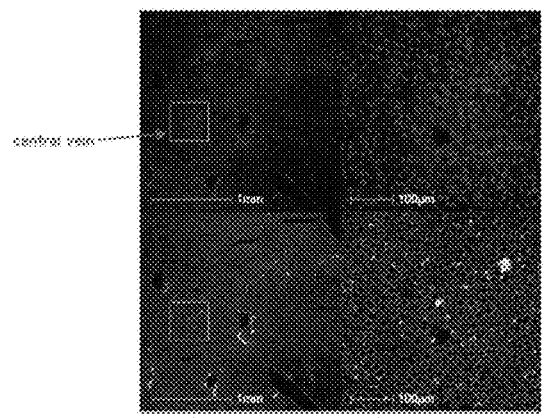
"LP1-hFIX" vector DNA/mRNA is visualized in red (FISH), hAAT RNA in purple (FISH), GS protein in blue (IHC), nuclei in grey (DAPI)
FIG. 3C
FIG. 3D
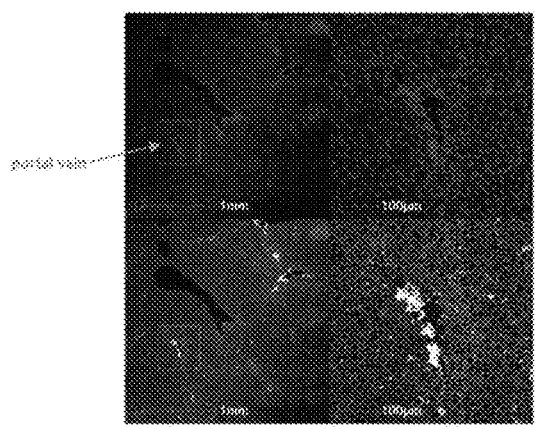
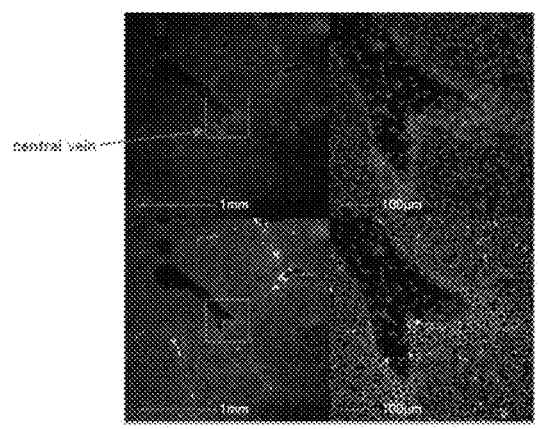
"LP1-hFIX" vector DNA/mRNA is visualized in red (FISH), hAAT RNA in purple (FISH), GS protein in blue (IHC), nuclei in grey (DAPI)

METHODS OF IMPROVING ADENO-ASSOCIATED VIRAL TRANSDUCTION

CROSS-REFERENCE TO RELATED APPLICATIONS

This application is a continuation of International Application No. PCT/EP2018/086487, filed Dec. 21, 2018, which claims the benefit of and priority to European Application No. 17210487.9, filed Dec. 22, 2017, both of which are hereby incorporated by reference herein in their entireties.

FIELD

Described herein are saturating agents, AAV gene therapy vectors, and therapeutic agents, as well as kits comprising the saturating agents, AAV gene therapy vectors, and therapeutic agents, and methods using the same.

BACKGROUND

The following discussion is provided to aid the reader in understanding the disclosure and is not admitted to describe or constitute prior art thereto.

The liver receives a blood supply from two sources. The first is the hepatic artery which delivers oxygenated blood from the general circulation. The second is the hepatic portal vein delivering deoxygenated blood from the small GI tract containing nutrients. Practically, the liver is supplied by both systemic and portal circulation; 20% of the blood comes from the hepatic artery and 80% from the portal vein. The blood flows through the liver tissue to the hepatic cells where many metabolic functions take place. The blood drains out of the liver via the hepatic vein. The liver tissue is not vascularized with a capillary network like most other organs, but rather consists of blood filled sinusoids surrounding the hepatic cells.

Upon entering the liver, the blood drains into the hepatic sinusoids, where it is screened by specialized cells to remove any pathogens that manage to get past the GI defenses. The plasma is filtered through the endothelial lining of the sinusoids and bathes the hepatocytes; these cells contain vast numbers of enzymes capable of breaking down and metabolizing most of the products that have been absorbed by the GI tract. The portal venous blood contains all the products of digestion absorbed from the GI tract, so all useful and non-useful products are processed in the liver before being either released back into the hepatic veins which join the inferior vena cava just inferior to the diaphragm, or stored in the liver for later use.

Therefore, liver sinusoids, connected directly to the portal circulation, serve as the first cellular barrier between the blood flow and the liver tissue. Liver sinusoids contain various cell types, including sinusoidal endothelial cells (LSECs/HSECs), Kupffer cells (liver residential macrophages), hepatic stellate cells (HSCs) and hepatic NK cells, all of which constitute the reticuloendothelial system (RES).

Studies on liver uptake of phage particles and adenovirus used in gene therapy have shown that the liver has a very high capacity to remove these particles from the circulation. It has been suggested that the RES plays a vital role in this clearance process. See, e.g., Kuzmin A et al., 1997, *Macrophage depletion increases the safety, efficacy and persistence of adenovirus-mediated gene transfer in vivo*, GENE THER 4: 309-316; Wolff G et al., 1997, *Enhancement of in vivo adenovirus-mediated gene transfer and expression by prior depletion of tissue macrophages in the target organ*, J VIROL 71: 624-629; and Schiedner G et al., 2003, *Selective depletion or blockade of Kupffer leads to enhanced and prolonged hepatic transgene expression using high-capacity adenoviral vectors*, MOL THER 7:35-43.

It has been suggested that parenterally administered lipid emulsions can block uptake of adenoviral vectors by the reticuloendothelial cells of the liver and potently increase transgene expression (Snoeys et al., 2006, *Lipid emulsions potently increase transgene expression in hepatocytes after adenoviral transfer*, MOL THER 13: 98-107). A similar strategy has been suggested to occupy the reticuloendothelial system of the liver, to prevent the deletion of nanoparticles (used for MRI in clinic) that are generally cleared by the RES. However, such an approach has never been suggested or attempted for adeno-associated viral (AAV) vectors, which may be used to transduce cells in the liver.

Indeed, AAV transduction is already perceived as very efficient, and therefore, there was little expectation that it could be further improved, let alone a motivation was provided to attempt to improve it. The present disclosure unexpected shows that AAV gene therapy can be significantly improved in terms of both transduction efficiency and safety by using saturating agents to occupy the RES response, thus allowing e.g. increasing hepatic uptake and transduction of the subsequently administered AAV.

SUMMARY OF INVENTION

Described herein are saturating agents, adeno-associated virus (AAV) gene therapy vectors, and therapeutic agents, and methods and kits using the same.

In one aspect, the present disclosure provides methods of treating a disease in a human subject, comprising: administering to a human subject suffering from a disease a saturating agent and an adeno-associated virus (AAV) gene therapy vector, wherein the saturating agent is taken up by one or more cells of a reticuloendothelial system (RES).

In one aspect, the present disclosure provides methods of treating a disease, comprising: administering a saturating agent and a gene therapy vector to a subject suffering from the disease, wherein the saturating agent is taken up by one or more cells of a reticuloendothelial system (RES), wherein the gene therapy vector does not comprise an adenovirus-based therapy, and wherein the disease is not cancer.

In one aspect, the present disclosure provides methods of treating a disease, comprising:
administering a saturating agent and an AAV gene therapy vector to a subject suffering from the disease, wherein the saturating agent is taken up by one or more cells of a reticuloendothelial system (RES).

In one aspect, the present disclosure provides methods of treating a disease, comprising: administering a saturating agent and an AAV gene therapy vector to a subject suffering from the disease, wherein the saturating agent is taken up by one or more cells of a reticuloendothelial system (RES).

In some embodiments of the foregoing aspects, the disease may include, but is not limited to, hemophilia, a genetic disorder or disease (e.g., Huntington's disease), a cardiovascular disease, or a neurological disease.

In one aspect, the present disclosure provides methods of increasing expression of a gene in a target organ or organ system, comprising: administering a saturating agent and an AAV gene therapy vector to a subject, wherein the saturating agent is taken up by one or more cells of a reticuloendothelial system (RES).

In some embodiments of the foregoing aspect, the target organ or organ system may be the liver; however, the target organ or organ system may also include the heart, lungs, brain/central nervous system, eyes, thyroid, pancreas, spleen, bladder, stomach, kidney, small intestine, lymph nodes, and/or prostate.

In one aspect, the present disclosure provides methods of increasing safety and/or efficacy of an AAV gene therapy comprising administering a saturating agent to a patient prior to administering an AAV gene therapy to the patient, thereby decreasing the necessary dose of the AAV gene therapy vector needed to achieve a therapeutically effective level of transduction and therefore increasing the safety and/efficacy of the AAV gene therapy compared to administering the AAV gene therapy vector alone.

In one aspect, the present disclosure provides kits comprising a saturating agent that is taken up by one or more cells of a reticuloendothelial system and an adeno-associated virus (AAV) gene therapy vector.

In one aspect, the present disclosure provides kits comprising a saturating agent and a therapeutic agent, wherein the saturating agent is taken up by one or more cells of a reticuloendothelial system (RES), wherein the therapeutic agent is an adeno-associated virus gene therapy vector.

In some embodiments of the foregoing aspects, the saturating agent comprises an emulsion, and in some embodiments, the emulsion is a lipid-based emulsion. In some embodiments, the lipid-based emulsion is selected from of INTRALIPID® 10%, INTRALIPID® 20%, and INTRALIPID® 30%. In some embodiments, the lipid-based emulsion is Clinolipid. In some embodiments, the lipid-based emulsion is selected from LIPOSYN®, LIPOSYN® II, and LIPOSYN® III.

In some embodiments of the foregoing aspects, the AAV gene therapy vectors may comprise an AAV capsid, a transgene, and/or a polynucleotide.

In some embodiments of the foregoing aspects, the AAV gene therapy vectors may comprise an AAV serotype selected from AAV1 or AAV5. In some embodiments, the AAV gene therapy vector may be a recombinant AAV (rAAV); for example, a rAAV2/5.

In some embodiments, the AAV gene therapy vector may be a chimeric AAV (AAV$^{ch}$); for example, a chimeric AAV serotype 5 (AAV5$^{ch}$).

In some embodiments of the foregoing aspects, the AAV gene therapy vectors may comprise a transgene that encodes a therapeutic protein or fragment thereof. For example, the therapeutic protein may be selected from factor IX (FIX), factor FVIII, interferon-β, neuropeptide Y receptor Y2, alpha glucosidase, C9orf72, superoxide dismutase, CFTR, chondroitinase, HEXA, and HEXB. In some embodiments, the therapeutic protein is a human protein or a recombinant protein.

In some embodiments, the AAV gene therapy vector encodes a therapeutic protein and/or therapeutic polynucleotide for the treatment, or prevention, of a disease of the liver. Suitable diseases for targeting the liver may be Glycogen storage disease type 1a, Citrullinemia Type 1, Phenylketonuria, Ornithine trancarbamylase deficiency, Hyperoxaluria type 1, Gaucher disease, MPDS VI, Fabry disease, Crigler Najjar Syndrome type 1, Propionic acidimia, Lysosomal acid lipase deficiency, Biotinase deficiency, Hereditary fructose intolerance, Abetalipoproteinaemia, Wilson disease, Niemann-Type C, homozygous familial hypcholesterolaemia, hepatitis virus B and hepatitis virus C.

In some embodiments of the foregoing aspects, the AAV gene therapy vectors may comprise a polynucleotide that encode interfering RNA (siRNA); a microRNA (miRNA); or a short hairpin RNA (shRNA).

The foregoing general description and following detailed description are exemplary and explanatory and are intended to provide further explanation of the invention.

BRIEF DESCRIPTION OF THE DRAWINGS

The patent or application file contains at least one drawing executed in color. Copies of this patent or patent application publication with color drawing(s) will be provided by the Office upon request and payment of necessary fee.

FIG. 2A shows the percentage of cells positive for hFIX vector DNA and mRNA. FIG. 2B shows the scoring of cells positive for hFIX vector DNA and mRNA, in which 1+=low, 2+=medium, 3+=strong, and 4+=very strong. FIG. 2C shows the H score of the cells positive for hFIX vector DNA and mRNA.

FIG. 3A shows the spatial distribution of AAV vector DNA/hFIX mRNA in relation to the portal vein in an animal receiving an intravenous injection of AAV5-LP1-hFIX (NHP 1002). FIG. 3B shows the spatial distribution of AAV vector DNA/hFIX mRNA in relation to the central vein in an animal receiving an intravenous injection of AAV5-LP1-hFIX (NHP 1002). FIG. 3C shows the spatial distribution of AAV vector DNA/hFIX mRNA in relation to the portal vein in an animal receiving an intravenous injection of AAV5-LP1-hFIX after pre-treatment with intralipid (NHP 2002). FIG. 3D shows the spatial distribution of AAV vector DNA/hFIX mRNA in relation to the central vein in an animal receiving an intravenous injection of AAV5-LP1-hFIX after pre-treatment with intralipid (NHP 2002).

DETAILED DESCRIPTION

Described herein are saturating agents, adeno-associated virus (AAV) gene therapy vectors, and therapeutic agents, as well as methods and kits comprising the same.

Figure 4A:
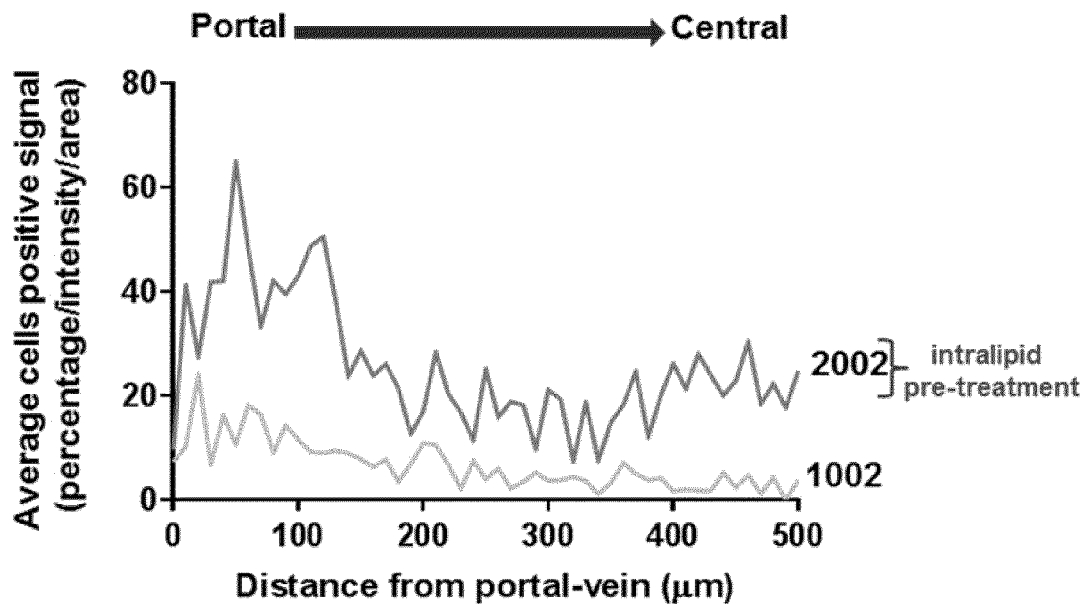
FIG. 4A shows the average cells positive signal (percentage/intensity/area: H score) relative to the distance to the portal.
Figure 4B:
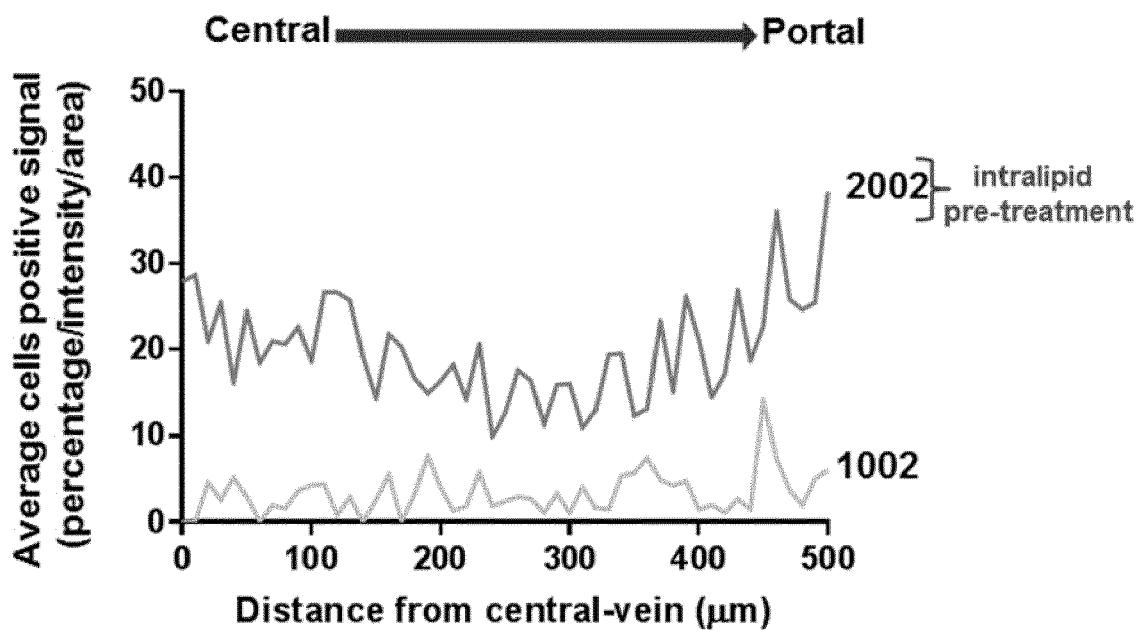
FIG. 4B shows the average cells positive signal (percentage/intensity/area: H score) relative to the distance to the central vein.

Without being bound by theory, the presently disclosed methods and kits utilize a saturation phenomenon to increase the transduction efficiency and safety of adeno-associated virus (AAV) gene therapy. While AAV gene therapy was traditionally considered efficient, particularly in regards to transduction of the liver, the present disclosure unexpectedly shows that by saturating the reticuloendothelial system (RES) via a pre-administration of a saturating agent, transduction efficiency of AAV gene therapy vectors into the liver, as well as other target organs and organ systems can be increased. This increase in transduction allows for a decrease in the actual dose of the AAV gene therapy vectors, which i.a. may increase safety by limiting the likelihood of an immunological response in the subject. The percentage of the liver that is transduced can be increased as well, allowing gene therapy treatments in humans that require a significant portion of the liver to be transduced. In addition, as shown in the example section, liver cells may now efficiently be transduced throughout the entire liver (see i.a. FIGS. 4A and 4B), wherein without the disclosed method, mainly cells close to the portal vein were transduced.

The disclosed methods may not be restricted to the treatment of the liver. Further organs that have an RES may be benefit as well. For example, lungs, kidney, spleen and small intestine may be targeted in an AAV gene therapy treatment and the disclosed methods of saturating the RES may improve the treatment of such organs as well. Furthermore, the disclosed methods may not only be advantageous in targeting organs having an RES. As the reticuloendothelial system (RES) may not be specific, any AAV treatment may benefit therefrom as it allows for the AAV vector to be more available for the organ targeted. For example, AAV targeted to a specific organ, e.g. to the central nervous system (i.a. the brain) or muscle, can be administered e.g. via the blood stream. Without being bound by theory, the RES cells may non-specifically scavenge much of the AAV from the bloodstream thereby limiting the availability of AAV to transduce the target organ. By subjecting the patient to the methods of the invention the availability of AAV can be improved thereby allowing more efficient transduction and/or lower amounts of AAV administered.

As discussed in more detail below, the type of AAV gene therapy vector is not particularly limited, and may include AAVs from various serotypes, as well as recombinant or chimeric AAVs. The saturating agent is similarly, unrestricted for the purposes of the present disclosure so long as the saturating agent is able to occupy the RES such that it is unable to clear the AAV particles. However, in many embodiments, the saturating agent is a lipid-based emulsion, such as the INTRALIPID® emulsion described herein.

The applications of the disclosed methods and phenomenon are far-reaching, and may be useful in improving the safety and efficacy of numerous gene therapy applications, as discussed in more detail below.

Definitions

As used in the description of the invention, clauses and clauses appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the term "saturating agent" refers to an agent that is capable of saturating the scavenger function of the RES. For the purposes of the present disclosure, precise compound or composition is not crucial, so long as the administration of the compound or composition can occupy the scavenging function of the RES such that the RES is unable to scavenge AAV gene therapy vectors that are concurrently or subsequently administered. While many saturating agents are emulsions, and more specifically lipid-based emulsions, the present disclosure provides more details relating to exemplary saturating agents below.

As used herein, the phrase "scavenger function of the RES" refers to the phagocytic activity of the RES. Kupffer cells are responsible for approximately 90% of the total phagocytic capacity of the RES. In some embodiments, the saturating agent is an agent that is capable of saturating the phagocytic capacity of the RES. In some embodiments, the saturating agent is an agent that is capable of saturating the phagocytic capacity of the Kupffer cells.

As used herein, the phrase "saturating the phagocytic capacity" refers to the phagocytic uptake of an agent (e.g., the saturating agent) that prevents the phagocytic cell from taking up another agent (e.g., the AAV gene therapy vector). Thus, in some embodiments, a saturating agent is an agent that is capable of saturating the phagocytic activity of the RES, such that the phagocytic cells of the RES take up the saturating agent instead of another agent, such as the AAV gene therapy vector and/or therapeutic agent. In some embodiments, a saturating agent is an agent that is capable of saturating the phagocytic activity of Kupffer cells, such that the Kupffer cells take up the saturating agent instead of another agent, such as the AAV gene therapy vector and/or therapeutic agent.

As used herein, the phrases "therapeutically effective amount" means a dose or plasma concentration in a subject that provides the specific pharmacological effect for which the disclosed AAV gene therapy vectors are administered, e.g. to express a therapeutic gene or gene of interest in a target cell/organ. It is emphasized that a therapeutically effective amount or therapeutic level of an AAV vector will not always be effective in treating the conditions described herein, even though such dosage is deemed to be a therapeutically effective amount by those of skill in the art. For convenience only, exemplary dosages, drug delivery amounts, and therapeutically effective amounts are provided below. Those skilled in the art can adjust such amounts in accordance with standard practices as needed to treat a specific subject and/or condition. The therapeutically effective amount may vary based on the route of administration and dosage form, the age and weight of the subject, and/or the disease or condition being treated.

As used herein, the terms "treatment" or "treating" refer to reducing, ameliorating or eliminating one or more signs, symptoms, or effects of a disease or condition (e.g., increasing expression of a coagulation factor in a subject with hemophilia, or decreasing expression of a gene is an associated with a disease, etc.).

The terms "individual," "subject," and "patient" are used interchangeably herein, and refer to any individual subject with a disease or condition in need of treatment. For the purposes of the present disclosure, the subject may be a primate, such as a human primate, or another mammal, such as a dog, cat, horse, pig, goat, or bovine, and the like.

Reticuloendothelial System

In some embodiments, the saturating agents disclosed herein are taken up by one or more cells of a reticuloendothelial system (RES). The one or more cells of a RES may include, but are not limited to, Kupffer cells, sinusoidal endothelial cells (SEC), and hepatic stellate cells (HSC). In some embodiments, the saturating agent may be taken up selectively or preferentially by any one of the aforementioned RES cell types, while in some embodiments, the saturating agent may be taken up by all of these cell types. In other words, the saturating agent may be taken up by one or more, two or more, or three or more cell types of the RES. For example, the saturating agent may be taken up selectively or preferentially by Kupffer cells and SECs, or it may be taken up selectively or preferentially Kupffer cells and HSCs or SECs and HSCs.

In some embodiments, the one or more cells of a RES comprise a plurality of cells. For example, at least 10%, 20%, 30%, 40%, 50%, 60%, 70%, 80%, 90%, 95% or more of the plurality of cells may be Kupffer cells. Additionally or alternatively, at least 10%, 20%, 30%, 40%, 50%, 60%, 70%, 80%, 90%, 95% or more of the plurality of cells may be sinusoidal endothelial cells (SECs). Additionally or alternatively, at least 10%, 20%, 30%, 40%, 50%, 60%, 70%, 80%, 90%, 95% or more of the plurality of cells may be hepatic stellate cells (HSCs).

In some embodiments, the saturating agent is primarily taken up by the one or more cells of a RES. For example, about 40-100%, about 50-90%, or about 60-80% of the saturating agent may be taken up by the one or more cells of the RES. Thus, at least 40%, at least 45%, at least 50%, at least 55%, at least 60%, at least 65%, at least 70%, at least 75%, at least 80%, at least 85%, at least 90%, or at least 95% or more of the saturating agent may be taken up by the one or more cells of a RES. In some embodiments, less than 10%, 20%, 30%, 40%, 50%, 55%, 60%, 65%, 70%, 75%, 80%, 85%, 90%, or 95% of the saturating agent is taken up by parenchymal liver cells.

As a result of the administration of a saturating agent, the amount of AAV gene therapy vectors that can be taken up by the RES is reduced. Accordingly, in some embodiments, less than 10%, less than 20%, less than 30%, less than 40%, less than 50%, less than 55%, less than 60%, less than 65%, less than 70%, less than 75%, less than 80%, less than 85%, less than 90%, or less than 95% of the AAV gene therapy vector and/or therapeutic agent may be taken up by the one or more cells of a RES. In some embodiments, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% or more of the AAV gene therapy vector and/or therapeutic agent is taken up by parenchymal liver cells or the target organ or organ system.

In some embodiments, the cells that primarily take up the saturating agent are different from the cells that primarily take up the AAV gene therapy vector and/or therapeutic agent. For example, in some embodiments, the saturating agent may be primarily taken up by non-parenchymal liver cells and the AAV gene therapy vector and/or therapeutic agent may be primarily taken up by parenchymal liver cells. In some embodiments, the saturating agent may be primarily taken up by the RES, while the AAV gene therapy vector and/or therapeutic agent is primarily taken up by a distinct target organ or organ system.

In some embodiments, the AAV gene therapy vector and/or therapeutic agent transduces at least 10%, at least 20%, at least 30%, at least 40%, at least 50%, at least 55%, at least 60%, at least 65%, at least 70%, at least 75%, at least 80%, at least 85%, at least 90%, or at least 95% or more of the cells in the target organ (e.g., parenchymal liver cells).

Saturating Agents

In some embodiments, the disclosed methods and kits comprise a saturating agent that is taken up by one or more cells of the RES when administered to a subject in need thereof.

In some embodiments, the subject may be administered a plurality of saturating agents that are taken up by one or more cells of the RES. For example, a subject may be administered at least one, at least two or at least three distinct saturating agents.

In some embodiments, the subject may be administered one or more doses of a saturating agent or a plurality of saturating agents. When more than one dose is administered to the subject, the respective doses may comprise the same saturating agents or different saturating agents.

In some embodiments, the saturating agent comprises one or more nutrients selected from carbohydrates, amino acids, lipids, vitamins, dietary minerals, or any combination thereof.

In some embodiments, the saturating agent comprises one or more lipids selected from triglycerides, steroids, phospholipids, or any combination thereof. In some embodiments, the phospholipids are selected from phosphatidylethanolamine, phosphatidylcholine, phosphatidylinositol, phosphatidylserine, lecithin, plasmalogen, and sphingomyelin. In some embodiments, the saturating agent comprises a phospholipid. In some embodiments, the phospholipid is phosphatidylcholine. In some embodiments, the phosphatidylcholine is selected from palmitoyl-oleyl-sn-phosphatidylcholine, 1-Oleoyl-2-palmitoyl-phosphatidylcholine, and L-α-phosphatidylcholine. In some embodiments, phosphatidylcholine is not L-α-phosphatidylcholine.

In some embodiments, saturating agent comprises a nutritional supplement selected from a total parenteral nutritional (TPN) supplement, peripheral parenteral nutrition (PPN) supplement, Aminosyn®, AMINOSYN®-HBC, AMINOSYN®-HF, AMINOSYN®-RF, BRANCHAMIN®, FREAMINE HBC®, FREAMINE® III, HEPATAMINE®, KABIVEN®, PERIKABIVEN®, NOVAMINE®, Premasol, PROCALAMINE®, ProSol, RENAMIN®, TROPHAMINE®, or any combination thereof.

In some embodiments, the saturating agent comprises an emulsion. Suitable emulsions may comprise soybean oil, vegetable oil, fish oil, phospholipids, and glycerol, or any combination thereof. The droplets of the emulsion may be larger than 0.1 µm or smaller than 2 µm, although emulsions with droplets outside of this size range may also have a saturating effect on the RES. In some embodiments, the emulsion comprises droplets having a size between 0.1 µm and 2 µm, between 0.5 and 1.5 µm, or between 0.75 and 1.25 µm. In some embodiments, the emulsion comprises a lipid emulsion (i.e., is a lipid-based emulsion) and/or a fat emulsion. It is understood that lipid emulsions may comprise fats and oils and may also be referred to as fat emulsions.

Exemplary emulsions can include, but are not limited to, INTRALIPID® 10%, INTRALIPID® 20%, and INTRALIPID® 30%, Clinolipid, LIPOSYN®, LIPOSYN® II, or LIPOSYN® III. Intralipid emulsions contain soybean oil, egg yolk phospholipids, glycerin, and water. For example, INTRALIPID® 10% contains 10% soybean oil, 1.2% egg yolk phospholipids, 2.25% glycerin, and water. INTRALIPID® 20% contains 20% soybean oil, 1.2% egg yolk phospholipids, 2.25% glycerin, and water. INTRALIPID® 30% contains 30% soybean oil, 1.2% egg yolk phospholipids, 2.25% glycerin, and water. Clinolipid emulsions contain refined olive oil and refined soybean oil in an approximate ratio of 4:1. For example, clinolipid 20% contains approximately 16% of olive oil, 4% of soybean oil, 1.2% egg phospholipids, 2.25% glycerin, 0.03% sodium oleate, and water. LIPOSYN® emulsions may be formulated as a 10% or 20% emulsion. LIPOSYN® II 10% contains 5% safflower oil, 5% soybean oil, up to 1.2% egg phosphatides added as an emulsifier and 2.5% glycerin in water. LIPOSYN® II 20% contains 10% safflower oil, 10% soybean oil, 1.2% egg phosphatides and 2.5% glycerin in water. LIPOSYN® III 10% contains 10% soybean oil, up to 1.2% egg phosphatides added as an emulsifier and 2.5% glycerin in water. LIPOSYN® III 20% contains 20% soybean oil, 1.2% egg phosphatides and 2.5% glycerin in water. One of skill in the art would understand that similar lipid and/or fat based emulsions can be prepared using other acceptable lipids and/or oils in similar percentages, and such emulsions would likewise be suitable for use in the disclosed methods.

In some embodiments, the saturating agent comprises a nanoparticle, such as a lipid nanoparticle (e.g., a liposome, micelle or reveres micelle). The nanoparticle may be a dispersed phase in an emulsion or an internal phase in a suspension. Exemplary nanoparticles may also include a micellar solution and solid lipid nanoparticle (SLN). For the purposes of the present disclosure, a nanoparticle generally has a diameter of between 0.2 to 300 nm.

Exemplary liposome that may be used as saturating agents can include, but are not limited to, an L-α-phosphatidylcholine liposome, a multilamellar vesicle (MLV), unilamellar vesicle, and cochleate vesicle. Those of skill in the art will understand that a unilamellar vesicle can be, for example, a small unilamellar vesicle (SUV) or a large unilamellar vesicle (LUV).

In some embodiments, the saturating agent may be a microsphere. In some embodiments, the saturating agent may be an empty viral capsid, such as an empty adenoviral capsid or an empty AAV capsid. In some embodiments, the saturating agent is not an empty viral capsid. AAV capsids, which include empty AAV capsids, have been suggested in the prior art in a pretreatment, to capture neutralizing components present in the blood such as e.g. neutralizing antibodies.

AAV Gene Therapy Vectors

In some embodiments, the disclosed methods and kits comprise an AAV gene therapy vector. In some embodiments, the disclosed kits and methods comprise a plurality of AAV gene therapy vectors. For example, the disclosed kits and methods may comprise at least one, at least two, or at least three AAV distinct AAV gene therapy vectors. When a subject is administered more than one AAV gene therapy vector, the vectors may be the same or different serotypes, and the vectors may encode the same or different therapeutic genes.

AAV gene therapy vectors may comprise an AAV capsid and a polynucleotide. The polynucleotide may encode a therapeutic protein; however, not all polynucleotides encode therapeutic proteins. In some embodiments, a polynucleotide within an AAV gene therapy vector may encode a gene of interest (e.g., a gene that is mutated in a subject), a protein of interest (e.g., a protein that is under-expressed or mutated in a subject), or a therapeutic RNA (e.g., a siRNA, miRNA, or shRNA that targets a gene that is mutated or overexpressed). Hence, the transgene or therapeutic gene may comprises a polynucleotide sequence that encodes a therapeutic protein or a therapeutic RNA or fragments thereof.

The serotype of the AAV gene therapy vector is not particularly limited and may include, but is not limited to, AAV serotype 1 (AAV1), AAV2, AAV3, AAV4, AAV5, AAV6, AAV7, AAV8, AAV9, AAV10, or AAV11. In some embodiments, the AAV is AAV1 or AAV5. In some embodiments, the AAV is AAV6, AAV7, AAV8, AAV9, or AAV10. In some embodiments, gene therapy may comprise administration of a plurality of AAV gene therapy vectors, and the vectors may be the same or different serotypes.

In some embodiments, the AAV was discovered in human cells or in non-human primate cells, such as rhesus cells or cynomolgus cells.

In some embodiments, the AAV capsid is not a wild-type capsid but is a recombinant AAV (rAAV), such as a rAAV2/5, which comprises at least a portion of AAV2 and AAV5. For example, the VP1 capsid protein may consist of a hybrid amino acid sequence between AAV2 and AAV5, whereas the VP2 and VP3 capsids may be derived from the AAV5 serotype (e.g. Urabe et al. *Scalable generation of high-titer recombinant adeno-associated virus type 5 in insect cells*. J Virol. 2006 February; 80(4):1874-85). In some embodiments, the AAV is a chimeric AAV (AAV$^{ch}$), such as a chimeric AAV serotype 5 (AAV5$^{ch}$).

When a plurality of AAV gene therapy vectors are administered to a subject, at least two of the plurality of AAV gene therapy vectors may be the same type of AAVs, while in some embodiments, at least two of the plurality of AAV gene therapy vectors may be different types of AAVs.

Therapeutic Genes

In some embodiments, the AAV gene therapy vectors comprise a transgene or therapeutic gene. The transgene or therapeutic gene comprises a polynucleotide sequence that encodes a therapeutic protein or a therapeutic RNA or fragments thereof.

The therapeutic protein may be a primate protein, a non-primate protein, or a human protein. In some embodiments, the therapeutic protein may include, but is not limited to, factor IX (FIX), factor VIII (FVIII) and modified forms thereof. In some embodiments, the therapeutic gene may include, but is not limited to, alpha-1 antitrypsin (AAT), aromatic amino acid decarboxylase (AADC), ATPase Sarcoplasmic/Endoplasmic Reticulum Ca2+ Transporting 2 (ATP2A2), cystic fibrosis transmembrane conductance regulator (CTFR), glutamic acid decarboxylase 65 kDa protein (GAD65), glutamic acid decarboxylase 67 kDa protein (GAD67), lipoprotein lipase (LPL), nerve growth factor (NGF), neurturin (NTN), porphobilinogen deaminase (PBGD), sarcoglycan alpha (SGCA), soluble fms-like tyrosine kinase-1 (sFLT-1), S100 calcium binding protein A1 (S100A1), survival of motor neuron 1 (SMN1), tripeptidyl peptidase 1 (TPP1), tumor necrosis factor receptor (TNFR)-immunoglobulin (IgG1) Fc fusion (TNFR:Fc), interferon beta (IFN-β), neuropeptide Y receptor Y2, alpha glucosidase, C9orf72, superoxide dismutase (SOD), CFTR, alpha-galactosidase, alpha-N-acetylgalactosaminidase, uricase, chondroitinase, HexA, HexB and modified forms thereof.

The transgenes and/or therapeutic genes may also relate to gene editing. Gene editing is a type of genetic engineering in which DNA is inserted, deleted or replaced in the genome of a living organism using engineered nucleases, or "molecular scissors". Currently four classes of gene editing may be utilized, which involves meganucleases, zinc finger nucleases (ZFNs), transcription activator-like effector-based nucleases (TALEN), and the clustered regularly interspaced short palindromic repeats CRISPR-Cas system. The AAV vectors utilized may be engineered such that the gene editing capabilities are transient to allow the endogenous gene to be edited. The nucleases create site-specific double-strand breaks (DSBs) at desired locations in the genome. The induced double-strand breaks are subsequently repaired through nonhomologous end-joining (NHEJ) or homologous recombination (HR), resulting in targeted mutations. For example, one or more AAV gene therapy vectors may encode a gene targeting a specific gene sequence. A targeted gene may be a diseased gene with the aim of the therapy being to disrupt expression of the diseased gene. Another approach may be with the aim to repair a diseased gene, e.g. with X-linked associated diseases or dominant disease associated genes. One or more AAV gene therapy vectors may encode for a gene editing sequence and a DNA sequence which is to be inserted/replace and/or to repair the gene associated with a disease via e.g. homologous recombination.

In some embodiments of the foregoing aspects, the AAV gene therapy vectors may comprise a polynucleotide that encode interfering RNA (siRNA); a microRNA (miRNA); or a short hairpin RNA (shRNA). In some embodiments, the siRNA, miRNA, or shRNA targets and silences or downregulates a gene associated with a disease. For example, well known target genes for silencing may include the Htt gene, the C9orf72 gene or the like, i.e. genes associated with repeat disorders (e.g. trinucleotide (i.e. polyglutamine or non-polyglutamine diseases) or hexanucleotide repeat disorders). In some embodiments, the therapeutic RNA interferes with the expression a gene that encodes a protein involved in a disease.

The therapeutic genes encoded by the AAV gene therapy vectors may be under the control of a promoter. Numerous suitable promoters are known in the art, and in some embodiments, the promoter may be a tissue specific promoter (such as a LP1 liver-specific promoter, a neurospecific promoter such as Neuron-Specific Enolase (NSE), human synapsin 1, caMK kinase and tubuline promoters). Constitutive promoters like the PGK promoter, CAG promoter or CMV promoter may also be used. Other suitable promoters that can be contemplated are inducible promoters, i.e. a promoter that initiates transcription only when the host cell is exposed to some particular stimulus. In any case, the skilled person is well capable of selecting an appropriate promoter for expression the therapeutic protein and/or therapeutic RNA.

Therapeutic Agents

In some embodiments, the disclosed methods and kits comprise one or more therapeutic agents that can be administers before, concurrently, or after administration of the saturating agent and/or AAV gene therapy vector.

Those of skill in the art will understand that additional therapeutic agents that are suitable for the disclosed methods and kits can include conventional therapies for the diseases and conditions disclosed herein.

Methods of Administration

The disclosed methods comprise administering a saturating agent and a AAV gene therapy vector. In some embodiments, the saturating agent and the AAV gene therapy vector are administered concurrently, while in some embodiments, the saturating agent and the AAV gene therapy vector are administered sequentially. The disclosed methods of administering a saturating agent and an AAV gene therapy vector may also be referred to as co-administering a saturating agent and an AAV gene therapy vector.

For example, the saturating agent may be administered prior to the AAV gene therapy vector. In some embodiments, the saturating agent is administered at least 5, 10, 15, 20, 25, 30, 35, 40, 45, 50, 55, 60, 65, 70, 75, 80, 85, 90, 95, 100, 110, 120, 130, 140, or 150 or more minutes prior to administration of the AAV gene therapy vector. In some embodiments, the saturating agent is administered at least 1, 2, 3, 4, 5, 6, 7, 8, 9, 10, 11, 12, 13, 14, 15, 16, 17, 18, 19, 20, 21, 22, 23, or 24 or more hours prior to administration of the AAV gene therapy vector. In some embodiments, the saturating agent is administered between 0.5 to 24 hours, between 0.5 to 12 hours, between 1 to 5 hours, or between 1 to 2 hours prior to administration of the AAV gene therapy vector. In some embodiments, the saturating agent is administered at least 1 hour prior to administration of the AAV gene therapy vector. In some embodiments, the saturating agent and the AAV gene therapy vector are administered within 24 hours or less of each other. In some embodiments, the saturating agent and the AAV gene therapy are administered within 48 hours or less of each other.

In some embodiments, two or more saturating agents may be administered to a subject, and the two or more saturating agents may be administered concurrently or sequentially.

In some embodiments, the first saturating agent may be administered at least 5, 10, 15, 20, 25, 30, 35, 40, 45, 50, 55, 60, 65, 70, 75, 80, 85, 90, 95, 100, 110, 120, 130, 140, or 150 or more minutes prior to administration of the one or more additional saturating agents. In some embodiments, the saturating agent is administered at least 1, 2, 3, 4, 5, 6, 7, 8, 9, 10, 11, 12, 13, 14, 15, 16, 17, 18, 19, 20, 21, 22, 23, or 24 or more hours prior to administration of the one or more additional saturating agents. In some embodiments, the first saturating agent may be administered prior to the AAV gene therapy vector and the one or more additional saturating agents are administered after the AAV gene therapy vector.

In some embodiments, the disclosed methods further comprise administering an additional therapeutic agent. In some embodiments, the AAV gene therapy vector and the one or more therapeutic agents are administered concurrently, while in some embodiments, they are administered sequentially. For example, the AAV gene therapy vector may be administered at least 5, 10, 15, 20, 25, 30, 35, 40, 45, 50, 55, 60, 65, 70, 75, 80, 85, 90, 95, 100, 110, 120, 130, 140, or 150 or more minutes prior to administration of the one or more therapeutic agents, or the AAV gene therapy vector may be administered at least 1, 2, 3, 4, 5, 6, 7, 8, 9, 10, 11, 12, 13, 14, 15, 16, 17, 18, 19, 20, 21, 22, 23, or 24 or more hours prior to administration of the one or more therapeutic agents. In some embodiments, the AAV gene therapy vector may be administered at least 5, 10, 15, 20, 25, 30, 35, 40, 45, 50, 55, 60, 65, 70, 75, 80, 85, 90, 95, 100, 110, 120, 130, 140, or 150 or more minutes after the administration of the one or more therapeutic agents, or the AAV gene therapy vector may be administered at least 1, 2, 3, 4, 5, 6, 7, 8, 9, 10, 11, 12, 13, 14, 15, 16, 17, 18, 19, 20, 21, 22, 23, or 24 or more hours after the administration of the one or more therapeutic agents.

The duration of the administration of the components of the disclosed methods may also vary. Indeed, a sustained infusion of a saturating agent or an AAV gene therapy vector may increase the efficacy of the respective components. Accordingly, in some embodiments, administration of the saturating agent may extend for at least 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 130, 140, or 150 or more minutes. In some embodiments, administration of the AAV gene therapy vector may extend for at least 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 130, 140, or 150 or more minutes. Similarly, when the disclosed methods further comprise administering an additional saturating agent or one or more therapeutic agents, administration of these components may extend for at least 1, 2, 3, 4, 5, 10, 15, 20, 25, 30, 35, 40, 45, 50, 55, 60, 65, 70, 75, 80, 85, 90, 95, 100, 110, 120, 130, 140, or 150 or more minutes.

In some embodiments, the methods disclosed herein comprise administering the saturating agent, AAV gene therapy vector, one or more additional saturating agents and/or one or more therapeutic agents systemically. Systemic administration may be enteral or parenteral. Suitable routes of enteral administration may include, but are not limited to, oral, sublingual, and rectal administration. Suitable routes of enteral administration may include, but are not limited to, inhalation, injection, and transdermal administration. For the purposes of the present disclosure, preferred routes of injection include intravenous, intramuscular, subcutaneous, intra-arterial, intra-articular, intrathecal, and intradermal injections.

In some embodiments, the saturating agent, AAV gene therapy vector, one or more additional saturating agents and/or one or more therapeutic agents are administered locally. Local administration can comprise intravenous, intramuscular, subcutaneous, intra-arterial, intra-articular, intrathecal, or intradermal injections at or near the target organ or organ system. For instance, when the lymph nodes are the target organ, the AAV gene therapy vectors may be administered in close proximity to a target lymph node. Similarly, if the disease being treated is a neurological disease, the AAV gene therapy vectors may be administered intrathecally. Other target organs or organ systems that may be suitably treated by locally administered AAV gene therapy vectors include, but are not limited to, the liver, lung, spleen, lymph nodes, kidney, small intestine, or brain.

In some embodiments, the route of administration for a first saturating agent is different from the route of administration for one or more additional saturating agents, while in some embodiments, any or all saturating agents may be administered via the same route.

In some embodiments, the route of administration for the saturating agent is different from the route of administration of the AAV gene therapy vector, while in some embodiments, the saturating agent and the AAV gene therapy vector are administered by the same route of administration.

In some embodiments, administering the saturating agent, therapeutic agent, one or more additional saturating agents, and/or one or more therapeutic agents comprises delivering the saturating agent, therapeutic agent, one or more additional saturating agents, and/or one or more therapeutic agents to an organ. In some embodiments, the organ is from an organ system selected from a musculoskeletal system, digestive system, respiratory system, urinary system, reproductive system, endocrine system, circulatory system, nervous system, and integumentary system. In some embodiments, the organ is selected from a brain, eye, thyroid, lung, heart, pancreas, liver, spleen, bladder, stomach, kidney, small intestine, lymph node, and prostate. In some embodiments, the organ is a liver. In some embodiments, the saturating agent, the AAV gene therapy vector, one or more additional saturating agents, and/or one or more therapeutic agents are delivered to one or more cells of the liver.

In some embodiments the disclosed methods comprise administering to a subject a fat-based emulsion and an AAV gene therapy vector. In some embodiments the disclosed methods comprise administering to a subject a lipid-based emulsion and an AAV gene therapy vector. In some embodiments, the emulsion is selected from of INTRALIPID® 10%, INTRALIPID® 20%, and INTRALIPID® 30%. In some embodiments, the emulsion administered is Clinolipid. In some embodiments, the emulsion administered is selected from LIPOSYN®, LIPOSYN® II, and LIPOSYN® III. The emulsion and the AAV gene therapy vector may be administered concurrently. The emulsion and the AAV gene therapy vector may also be mixed prior to administration. The emulsion may be administered prior to the AAV gene therapy vector administration. At least 1, 2, 3, 4, 5, 6, 7, 8, 9, 10, 11, 12, 13, 14, 15, 16, 17, 18, 19, 20, 21, 22, 23, or 24 or more hours prior to administration of the AAV gene therapy vector, the emulsion may be administered. For example, the dosage and/or route of administration as shown in the example section of an emulsion such as Intralipid, or the like, resulted in a triglyceride level as measured in the blood plasma of above 1.33 mmol/L or higher, which improved transduction. Any dosage and/or route of administration may be selected in order to achieve a triglyceride level in the blood of at least 2 mmol/L, 3 mmol/L, 4 mmol/L, 5 mmol/L, 6 mmol/L, 7 mmol/L, 8 mmol/L, 9 mmol/L, 10 mmol/L or more. In other words, a method is provided herein wherein a subject is treated with a food supplement, such as a lipid and/or fat based emulsion formulation (e.g. Intralipid), thereby achieving a triglyceride level in the blood of at least 2 mmol/L, 3 mmol/L, 4 mmol/L, 5 mmol/L, 6 mmol/L, 7 mmol/L, 8 mmol/L, 9 mmol/L, 10 mmol/L or more, followed by subsequent administration of an AAV gene therapy vector. The dosage of the emulsion selected may hence be for example, 0.5 g/kg, 1 g/kg, 1.5 g/kg, 2 g/kg, 2.5 g/kg, 3 g/kg, 3.5 g/kg, 4 g/kg, 4.5 g/kg, 5 g/kg, 5.5 g/kg, 6 g/kg, 6.5 g/kg, 7 g/kg, 7.5 g/kg, 8 g/kg, 8.5 g/kg, 9 g/kg, 9.5 g/kg, or 10 g/kg or more. In some embodiments, the dosage of the emulsion may be less than 5 g/kg, 5.5 g/kg, 6 g/kg, 6.5 g/kg, 7 g/kg, 7.5 g/kg, 8 g/kg, 8.5 g/kg, 9 g/kg, 9.5 g/kg, or 10 g/kg. In some embodiments, the dosage of the emulsion is between 0.5 g/kg and 5 g/kg. In some embodiments, the dosage of the emulsion is about 2 g/kg or about 4 g/kg.

Doses and Dosage Forms

In some embodiments, the disclosed kits and methods comprise a specific dosage of a saturating agent. The dosage of the saturating agent may be, for example, 0.5 g/kg, 1 g/kg, 1.5 g/kg, 2 g/kg, 2.5 g/kg, 3 g/kg, 3.5 g/kg, 4 g/kg, 4.5 g/kg, 5 g/kg, 5.5 g/kg, 6 g/kg, 6.5 g/kg, 7 g/kg, 7.5 g/kg, 8 g/kg, 8.5 g/kg, 9 g/kg, 9.5 g/kg, or 10 g/kg or more. In some embodiments, the dosage of the saturating agent may be less than 5 g/kg, 5.5 g/kg, 6 g/kg, 6.5 g/kg, 7 g/kg, 7.5 g/kg, 8 g/kg, 8.5 g/kg, 9 g/kg, 9.5 g/kg, or 10 g/kg. In some embodiments, the dosage of the saturating agent is between 0.5 g/kg and 5 g/kg. In some embodiments, the dosage of the saturating agent is about 2 g/kg or about 4 g/kg. When more than one saturating agent is administered to a subject, the respective dosages may be the same or different.

As long as a dosage and/or route of administration is selected for the saturating agent that can achieve substantial saturation of the RES cells that allows for improved transductions, such a dosage and/or route is contemplated. For example, the dosage and/or route of administration as shown in the example section of a saturating agent and/or emulsion such as Intralipid, or the like, resulted in a triglyceride level as measured in the blood plasma of above 1.33 mmol/L or higher, improved transduction may be obtained (see e.g. FIG. 8A). The dosage and/or route of administration may be selected to achieve a triglyceride level in the blood of at least 2 mmol/L, 3 mmol/L, 4 mmol/L, 5 mmol/L, 6 mmol/L, 7 mmol/L, 8 mmol/L, 9 mmol/L, 10 mmol/L or more. In other words, a method is provided herein wherein a subject is treated with a food supplement, such as a lipid based emulsion formulation (e.g. Intralipid), thereby achieving a triglyceride level in the blood of at least 2 mmol/L, 3 mmol/L, 4 mmol/L, 5 mmol/L, 6 mmol/L, 7 mmol/L, 8 mmol/L, 9 mmol/L, 10 mmol/L or more, followed by subsequent administration of an AAV gene therapy vector.

In some embodiments, the disclosed kits and methods comprise a specific dosage of an AAV gene therapy vector. The dosage of the AAV gene therapy vector may be, for example, $1\times10^{10}$ gc/kg, $5\times10^{10}$ gc/kg, $1\times10^{11}$ gc/kg, $5\times10^{11}$ gc/kg, $1\times10^{12}$ gc/kg, $2\times10^{12}$ gc/kg, $3\times10^{12}$ gc/kg, $4\times10^{12}$ gc/kg, $5\times10^{12}$ gc/kg, $6\times10^{12}$ gc/kg, $7\times10^{12}$ gc/kg, $8\times10^{12}$ gc/kg, $9\times10^{12}$ gc/kg, $1\times10^{13}$ gc/kg, $5\times10^{13}$ gc/kg, $1\times10^{14}$ gc/kg, $5\times10^{14}$ gc/kg, or $1\times10^{15}$ gc/kg or more. In some embodiments, the dosage of the AAV gene therapy vector is less than $1\times10^{13}$ gc/kg, $5\times10^{13}$ gc/kg, $1\times10^{14}$ gc/kg, $5\times10^{14}$ gc/kg, or $1\times10^{15}$ gc/kg. In some embodiments, the dosage of the AAV gene therapy vector is between $1\times10^{12}$ gc/kg and $1\times10^{14}$ gc/kg. In some embodiments, the dosage of the AAV gene therapy vector is between $5\times10^{12}$ gc/kg and $5\times10^{13}$ gc/kg. In some embodiments, the dosage of the AAV gene therapy vector is $4\times10^{12}$ gc/kg, $4.5\times10^{12}$ gc/kg, $5\times10^{12}$ gc/kg, $5.5\times10^{12}$ gc/kg, $6\times10^{12}$ gc/kg, $6.5\times10^{12}$ gc/kg, $7\times10^{12}$ gc/kg, $7.5\times10^{12}$ gc/kg, $8\times10^{12}$ gc/kg, $8.5\times10^{12}$ gc/kg, $8.6\times10^{12}$ gc/kg, $8.7\times10^{12}$ gc/kg, $8.8\times10^{12}$ gc/kg, $8.9\times10^{12}$ gc/kg, $9\times10^{12}$ gc/kg, $9.1\times10^{12}$ gc/kg, $9.2\times10^{12}$ gc/kg, $9.3\times10^{12}$ gc/kg, $9.4\times10^{12}$ gc/kg, $9.5\times10^{12}$ gc/kg, $9.6\times10^{12}$ gc/kg, $9.7\times10^{12}$ gc/kg, $9.8\times10^{12}$ gc/kg, $9.9\times10^{12}$ gc/kg, $1\times10^{13}$ gc/kg, $1.5\times10^{13}$ gc/kg, $2\times10^{13}$ gc/kg, $2.5\times10^{13}$ gc/kg, $3\times10^{13}$ gc/kg, $3.5\times10^{13}$ gc/kg, $4\times10^{13}$ gc/kg, $4.5\times10^{13}$ gc/kg, $5\times10^{13}$ gc/kg, $5.5\times10^{13}$ gc/kg, or $6\times10^{13}$ gc/kg or more. In some embodiments, the dosage of the AAV gene therapy vector is about $9.7\times10^{12}$ gc/kg or about $5\times10^{13}$ gc/kg. In some embodiments, the dosage of the AAV gene therapy vector is inversely proportional to the dosage of the saturating agent. When more than one AAV gene therapy vector is administered to a subject, the respective dosages may be the same or different.

In some embodiments, the dose of an AAV gene therapy vector is less when co-administered with a saturating agent compared to the dose of the same AAV gene therapy vector when administered without the saturating agent. In some embodiments, co-administration with the saturating agent results in at least about a 5%, 10%, 15%, 20%, 25%, 30%, 35%, 40%, 45%, 50%, 55%, 60%, 65%, 70%, or 75% reduction in the dose of the AAV gene therapy vector as compared to the dose of the AAV gene therapy vector without co-administration of the saturating agent.

Increased Transduction Efficiency and Reduced Side Effects

Co-administration of a saturating agent, either concurrently or sequentially, with an AAV gene therapy vector decreases the amount of uptake of the AAV gene therapy vector by the RES. As a result of this decrease in RES sequestration, more AAV gene therapy vectors can stay in circulation for longer, allowing larger amounts of the AAV gene therapy vector to reach the target cell, organ, or organ system. The increased amount of AAV gene therapy vector reaching the target cell, organ, or organ system likewise leads to increased transduction efficiency.

Due to this increased transduction efficiency, the therapeutically effective amount of AAV gene therapy vectors needed to treat a given disease can be reduced relative to the amount that would be needed to treat the same disease without co-administration of a saturating agent. Unintended immunological responses are the most likely serious side effect that may occur as a result of administering an AAV gene therapy vector to a subject, and decreasing the amount of AAV gene therapy vectors administered to a subject will decrease the likelihood of these unintended side effects.

Accordingly, in some embodiments, co-administration of a saturating agent and an AAV gene therapy vector improves the transduction efficiency of the AAV gene therapy vector by at least about 10%, 15%, 20%, 25%, 30%, 35%, 40%, 45%, 50%, 55%, 60%, 65%, 70%, 75%, 80%, 85%, 90%, 95%, or 100% or more as compared to the transduction efficiency of the AAV gene therapy vector without co-administration of the saturating agent. More specifically, the disclosed methods may increase transduction efficiency by at least about 30% or more as compared to the transduction efficiency without co-administration of the saturating agent. In some embodiments, the transduction efficiency of the disclosed methods is increased by at least about 1.5, 2, 2.5, 3, 3.5, 4, 4.4, 5, 5.5, 6, 6.5, 7, 7.5, 8, 8.5, 9, 9.5, or 10-fold or more as compared to the transduction efficiency of methods without co-administration of a saturating agent. More specifically, the disclosed methods may increase transduction efficiency by at least about 2-fold or 3-fold or more as compared to the transduction efficiency of without co-administration of a saturating agent.

In some embodiments, transduction efficiency can be measured based on the level of transgene expression, for example, by detecting the level of a therapeutic protein encoded by the AAV gene therapy vector. The therapeutic protein may be detected by any protein detection method known in the art, including, but not limited to, fluorometry, calorimetry, luminescence, gels, blots, and arrays. In some embodiments, the therapeutic protein is detected by enzyme-linked immunosorbent assay (ELISA).

In some embodiments, the transduction efficiency can be measured based on the transgene copy number. The transgene copy number can be determined by any gene copy number method known in the art, including, but not limited to, Southern blotting, polymerase chain reaction (PCR), and fluorescence in situ hybridization (FISH). In some embodiments, the transgene copy number is measured by quantitative PCR (qPCR).

In some embodiments, co-administration of the saturating agent with the AAV gene therapy vector and/or therapeutic agent results in a reduction of one or more side effects caused by the AAV gene therapy as compared to administration of the AAV gene therapy without a saturating agent. The reduction in one or more side effects can include reducing the severity of one or more side effects or preventing the one or more side effects from occurring altogether.

In some embodiments, a side effect of the AAV gene therapy is the generation of an immunological response. The immunological response may be a humoral immune response, such as a humoral response caused by the viral capsid or the therapeutic protein or RNA encoded by the AAV gene therapy vector. In some embodiments, reducing the side effect comprises an antibody response or a cellular immune response.

In some embodiments, co-administration of the saturating agent with the AAV gene therapy vector results in an increased half-life of the AAV gene therapy vector as compared to administration of the AAV gene therapy without a saturating agent. The half-life of the AAV gene therapy vector can be calculated based on the clearance rate of the AAV gene therapy vector from the blood. In some embodiments, the blood clearance rate of the AAV gene therapy vector in the disclosed methods is decreased compared to administration without the saturating agent. In some embodiments, the duration of the AAV gene therapy vector in the blood is increased when co-administered with the saturating agent as compared to without the saturating agent. In some embodiments, the amount of the AAV gene therapy vector in the blood is increased when administered with the saturating agent as compared to without the saturating agent.

In some embodiments, co-administration of the saturating agent with the AAV gene therapy vector increases the bio-distribution of the AAV gene therapy vector as compared to administration of the AAV gene therapy vector and/or therapeutic agent without the saturating agent. In some embodiments, increasing the bio-distribution comprises increasing the amount of the AAV gene therapy vector in a target cell, organ, tissue, or organ system. In some embodiments, increasing the bio-distribution comprises increasing the amount of the AAV gene therapy vector in the interior region of an organ or tissue. In some embodiments, the amount of the AAV gene therapy vector in the organ or tissue is based on the detection of the AAV gene therapy vector in the organ or tissue. In some embodiments, detection of the AAV gene therapy vector comprises detection of the viral capsid, detection of the therapeutic gene or fragment thereof, or detection of the therapeutic protein.

Indications

The disclosed methods and kits can be used for treating genetic disorders and diseases. Genetic diseases and disorders that may be treated with the disclosed methods and kits include, but are not limited to, acute intermittent *Porphyria* (AIP), age-related macular degeneration, amyotrophic lateral sclerosis, cystic fibrosis, paralysis, Alzheimer's disease, Parkinson's disease, Huntington's disease, arthritis, Batten disease, Canavan disease, Citrullinemia type 1, Crigler Najjar, hemophilia, rheumatoid arthritis, epilepsy, congestive heart failure, cystic fibrosis, Duchene muscular dystrophy, dyslipidemia, glycogen storage disease type I (GSD-I), hemophilia A, hemophilia B, hereditary emphysema, homozygous familial hypercholesterolemia (HoFH), Huntington's disease (HD), Leber's congenital amaurosis, methylmalonic academia, ornithine transcarbamylase deficiency (OTC), Parkinson's disease, phenylketonuria (PKU), spinal muscular atrophy, paralysis, Wilson disease, epilepsy, Pompe disease, amyotrophic lateral sclerosis (ALS), Tay-Sachs disease, hyperoxaluria (PH-1), spinocerebellar ataxia type 1 (SCA-1), SCA-3, u-dystrophin, Gaucher's types II or III, arrhythmogenic right ventricular cardiomyopathy (ARVC), Fabry disease, familial Mediterranean fever (FMF), proprionic acidemia, fragile X syndrome, Rett syndrome, Niemann-Pick, and Krabbe disease.

In some embodiments, the AAV gene therapy vectors may be for the treatment of lysosomal storage disorders, metabolic disorders and clotting disorders.

Lysosomal storage disorders disorders may result from a lack of specific enzymes that break down certain lipids (fats) or carbohydrates (sugars) in the body cells. Because the body cannot break down the fat or carbohydrate targeted by enzymes for recycling, these may accumulate in cell lysosomes disrupting normal function resulting in lysosomal storage disorders. Lysosomal disorders may include may include Farber disease, Krabbe disease (Infantile or late onset), Galactosialidosis, Fabry disease (alpha-galactosidase A), Schindler disease (alpha-galactosidase B), Beta-galactosidase/GM1 gangliosidosis, GM2 gangliosidosis, Gaucher disease Type I, II and III, Sphingomyelinase, Lysosomal acid lipase deficiency, Niemann-Pick disease Type A and B, Sulfatidosis, Saposin B deficiency, Multiple sulfatase deficiency, Mucopolysaccharidoses Types I (Hurler/Scheie), II (Hunter), III (Sanfilippo), IV(Morquio), VI (Maroteaux), VII (Sly) and IX (Hyaluronidase deficiency), Mucolipidosis Types I, II, III and IV, Niemann-Pick disease, Neuronal ceroid lipofuscinoses Type 1, 2, 3, 4, 5, 6, 7, 8, 9, and 10, Wolman disease, Alpha-mannosidosis, Beta-mannosidosis, Aspartylglucosaminuria, Fucosidosis, Lysosomal transport diseases, Cystinosis, Pycnodysostosis, Salla disease, Infantile free sialic acid storage disease, Glycogen storage diseases such as Pompe disease and Danon disease, Cholesteryl ester storage disease.

Metabolic disorders may include ornithine transcarbamylase deficiency, phenylketonuria, propionic acidemia, methylmalonic acidemia, primary hyperoxaluria.

Clotting disorders may include deficiencies in coagulation Factors, VII, VIII, IX and X, XI, V, XII, II, von Willebrand factor, combined FV/FVIII deficiency, thalassemia.

For example, in some embodiments, hemophilia A or B can be treated using the disclosed methods by administering to a subject a saturating agent (e.g., a lipid-based emulsion) and subsequently administering an AAV gene therapy vector that encodes FIX, or a variant thereof. In some embodiments, the AAV gene therapy vector may be an AAV5 serotype and the therapeutic gene (i.e., a gene encoding FIX) may be under the control of a liver-specific promoter (e.g., LP-1). Moreover, in some embodiments, the therapeutic FIX protein may comprise one or more insertions, deletions, or substitutions, such as described i.a. in [reference i.a. Simioni, Blutspende and several others, Spark)

EXAMPLES

Example 1—Analysis of Intralipid Pre-Treatment in Animals Treated with AAV Gene Therapy Vector In this example, the effect of intralipid pre-treatment in animals treated with adeno-associated virus (AAV) gene therapy was analyzed. Specifically, the effect of Intralipid 20%, an FDA approved nutritional supplement, pretreatment on AAV-vector transduction efficacy in the liver and subsequently, transgene expression was investigated. In addition, the effects of an Intralipid 20% pre-treatment on AAV bio-distribution and anti-AAV immune responses were analyzed.

Experimental set-up: Non-human primates (NHPs, n=2) that tested negative for the presence of anti-AAV serotype 5 neutralizing antibodies (NABs) were injected intravenously with a bolus of Intralipid 20% at the clinical dose (i.e., 2 g/kg) one hour before intravenous administration of the AAV gene therapy vector (e.g., AAV5(160)-LP1-hFIX) at a dose of $9.7 \times 10^{12}$ gc/kg (referred to as intralipid pre-treated animals). A control group (n=2) was injected with AAV5 (160)-LP1-hFIX at a dose of $9.7 \times 10^{12}$ gc/kg without Intralipid 20% pre-treatment. The animals were monitored for 8 weeks before sacrifice. Blood samples were taken at 1 hour, 4 hours, 8 hours, 24 hours, 4 days, and weekly after AAV administration. Tissues were collected at time of sacrifice for further analysis. The negative controls were blood/plasma samples taken before any treatment and tissues from control animals (previous internal studies).

| Animals | Pre-existing NAB | Intralipid Bolus injection (day 0 of the exp.) | AAV injection (1 hour after Intralipid injection) |
| --- | --- | --- | --- |
| Group 1 (2 animals) | No | Yes | AAV5-LP1-hFIX 9.7 × 10$^{12}$ gc/kg |
| Group 2 (2 animals) | No | No | AAV5-LP1-hFIX 9.7 × 10$^{12}$ gc/kg |

Results

Transduction Efficacy: Transgene Protein Expression and Vector DNA Copies in Liver To determine the effect of pre-treatment with Intralipid 20% on the efficacy of liver transduction by AAV5-LP1-hFIX, the levels of hFIX transgene expression were analysed in monkey plasma samples. The hFIX protein levels were measured by ELISA in plasma samples collected at 4, 8, 14, 21, 28, 42 and 56 after AAV5-LP1-hFIX administration. In addition, the AAV vector DNA copies numbers in liver tissue were determined at time of sacrifice by quantitative polymerase chain reaction (QPCR).

Figure 1A:
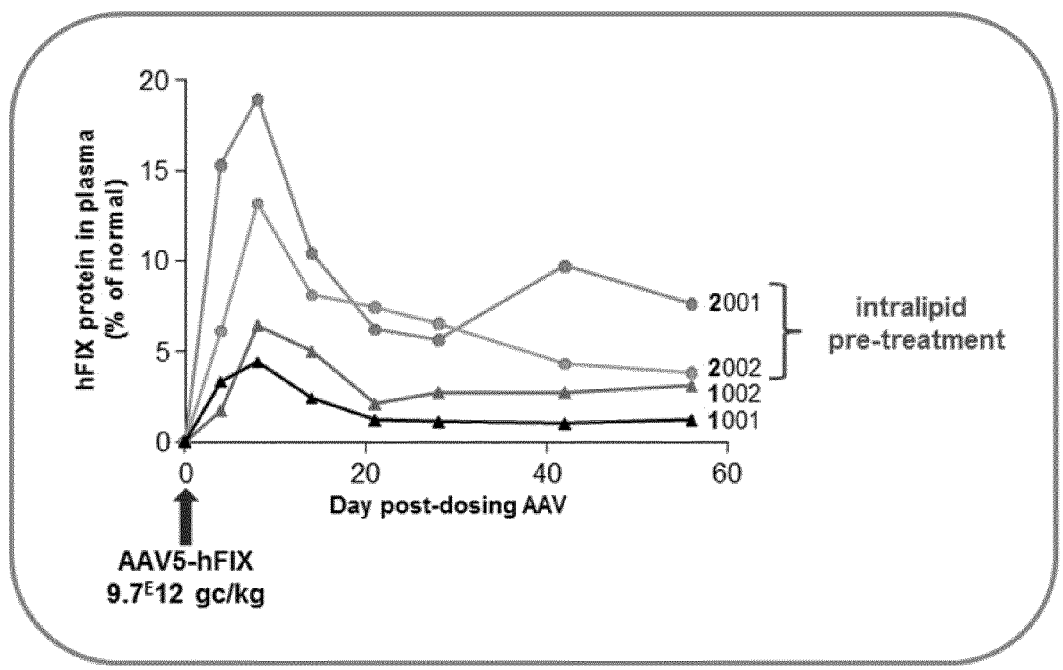
FIG. 1A shows the effect of Intralipid pre-treatment on hFIX transgene protein levels in plasma.

As shown in FIG. 1A, an increase in the levels of transgene expression was observed in the animals injected with AAV5-hFIX after intralipid bolus (see 2001 and 2002) when compared to the control group (see 1001 and 1002), with an average increase of 3.4 fold.

Figure 1B:
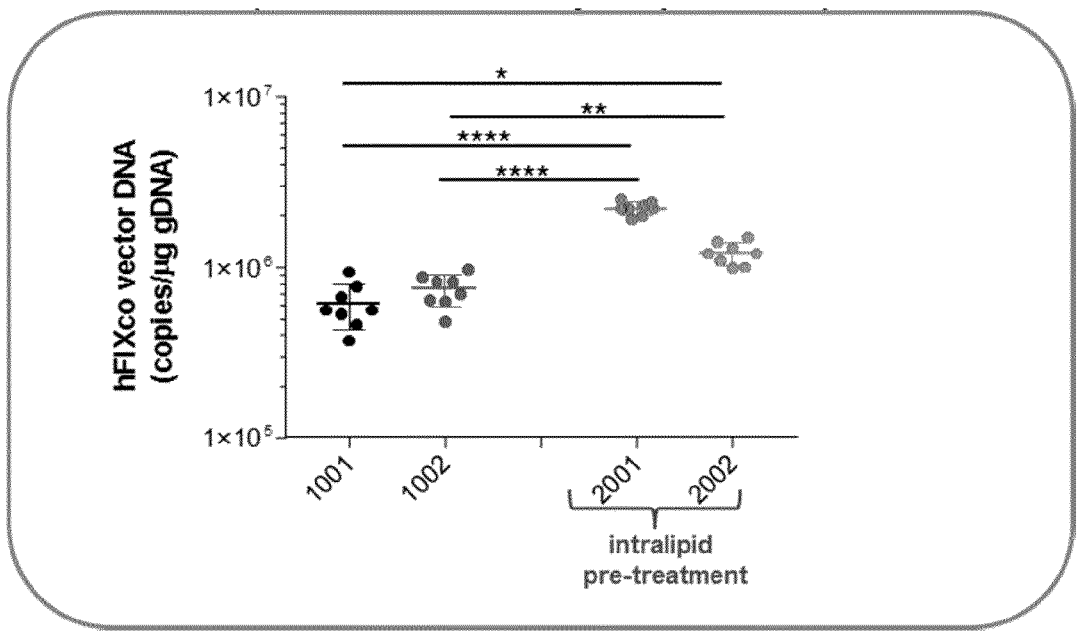
FIG. 1B shows the effect of Intralipid pre-treatment on AAV vector DNA copies in liver tissue.

Accordingly, as shown in FIG. 1B, the vector DNA copies numbers were higher in the animals pre-treated with intralipid than in the control group, with an average increase of 2.6 fold.

Overall, the data obtained indicated an improvement in liver transduction efficacy by AAV gene therapy and a subsequent increase in the levels of circulating transgene protein in animals pre-treated with Intralipid 20%.

Transduction Efficacy and Spatial Distribution (FISH)

To further investigate the transduction efficacy and spatial distribution of AAV gene therapy in the liver tissue, the presence of AAV vector DNA and transgene RNA were detected in liver tissue samples by fluorescent in situ hybridization (FISH). The assay was performed with a probe that hybridized to both AAV-hFIX vector DNA and hFIX mRNA. To assess the quality of the tissue and procedure, a liver positive (alpha 1 anti-trypsin, hAAT) and a negative (DapB) control probes were used in the assay. In addition to the probes, the tissues were stained with DAPI to visualize the cell-nucleus and an antibody against glutamine synthetase (GS) to visualize the central vein.

The images obtained were analyzed with image analysis software (Halo, IndicalLab). From the acquired images, an average of 4000 cells from each liver tissue were analyzed. The analysis was based on the percentage of cells positive for AAV vector DNA and transgene RNA and scoring of cells positive for AAV vector DNA and transgene RNA (see FIGS. 2A and 2B, respectively). The cells positive for the probes were scored low (1+), medium (2+), strong (3+), or very strong (4+) based on the combination of average positive signal area [μm$^2$] and average intensity of positive signal within cell. In addition, the H-score of cells positive for AAV vector DNA and transgene RNA, a semi-quantitative score system which calculates a score from 0 to 300 based on both the intensity of cell staining and the percentage of cells stained, was determined for each animal (see FIG. 2C).

Figure 2A:
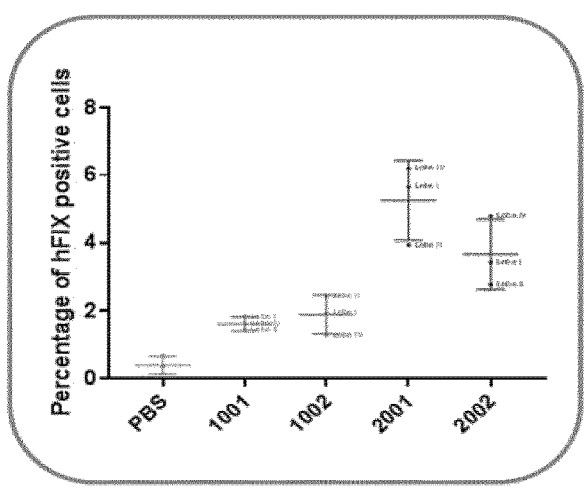
FIGS. 2A-2C show the effect of intralipid pre-treatment on AAV5-LP1-hFIX transduction efficacy.
Figure 2B:
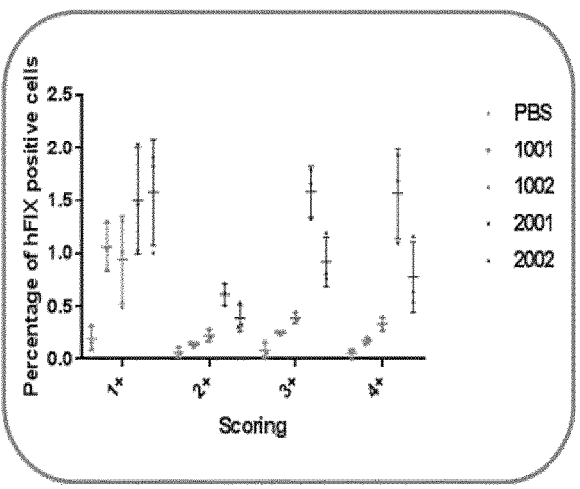
Figure 2C:
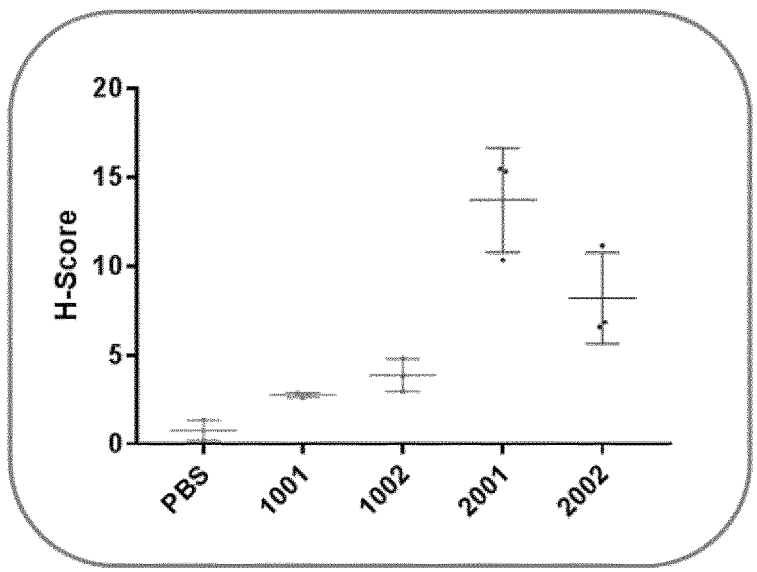

As shown in FIG. 2A-2C, a significantly higher number of liver cells were transduced by AAV5 after pre-treatment with Intralipid 20% when compared to the control animals. The average number of positive cells per animal group were found divided through the +1, +2, +3, +4 categories and account for the H score values. The H score is an histochemical data analysis method used in cancer diagnostics (Hirsch et al., J Clin Oncol 21:3798-3807, 2003 and John et al. Oncogene 28:S14-S23, 2009). An H score applies an algorithm to give more weight to cells more intensely stained, which was applied to the GFP transgene expression scored.

The percentage of cells positive for AAV vector DNA and transgene RNA was, on average, 2.55 times (overall percentage) or 3.2 times (H score) higher in intralipid pre-treated animals. According to these results, the H score reflected more accurately the levels of circulating hFIX measured than the overall cell percentage.

These experiments also show the beneficial effect of intralipid pre-treatment on AAV5-LP1-hFIX spatial distribution in liver tissue (FIGS. 3A-3D). The presence of AAV vector DNA/transgene hFIX mRNA was analyzed by fluorescent in situ hybridization with a probe that hybridized to both AAV-hFIX vector DNA and hFIX mRNA. The images obtained were analyzed with image analysis software (Halo, IndicalLab) and the spatial distribution was determined in relation to general liver morphology.

The spatial distribution of AAV vector DNA/hFIX mRNA were analysed in relation to the portal veins (FIGS. 3A and 3C) and central veins (FIGS. 3B and 3D). After intravenous injection of AAV5-LP1-hFIX, the AAV vector DNA/hFIX mRNA was mostly detected around the portal vein with very limited spreading into the liver tissue (FIGS. 3A and 3B, control animal NHP 1002). Interestingly, after Intralipid 20% pre-treatment, the diffusion of the AAV vector DNA/hFIX mRNA in the liver tissue was increased (FIGS. 3C and 3D, intralipid pre-treatment animal NHP 2002). Furthermore, the AAV vector DNA/hFIX mRNA found localized around both portal and central veins indicated an increased diffusion in the tissue (FIGS. 3C and 3D, intralipid pre-treatment animal NHP 2002).

Graphical representations of the effect of intralipid pre-treatment on AAV5-LP1-hFIX spatial distribution in liver tissue are shown in FIGS. 4A and 4B. FIG. 4A shows the average cells positive signal (percentage/intensity/area: H score values) in relation with distance to the portal vein (e.g., distance from central vein to portal vein) for the control animal (1002) and the Intralipid 20% pre-treated animal (2002). FIG. 4B shows the average cells positive signal (percentage/intensity/area: H score values) in relation with distance to the central vein (e.g., distance from portal vein to central vein) for the control animal (1002) and the animal pre-treated with Intralipid 20 (2002).

Figure 5A:
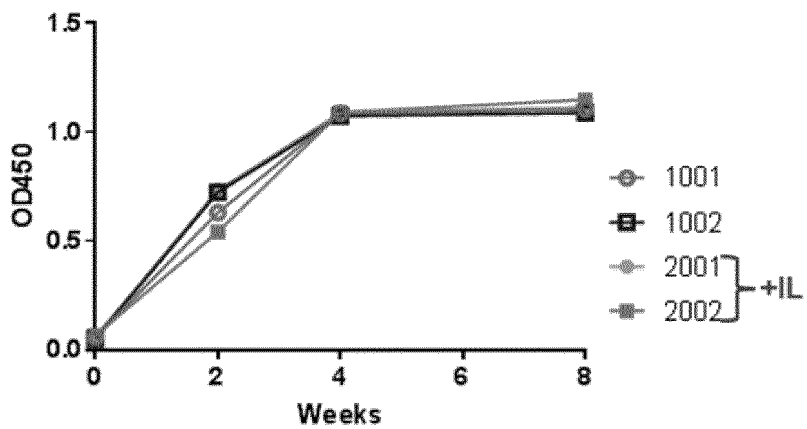
FIG. 5A shows the humoral immune response in control animals (1001, 1002) and intralipid pre-treated animals (2001, 2002), as measured by levels of anti-AAV total antibodies.
Figure 5B:
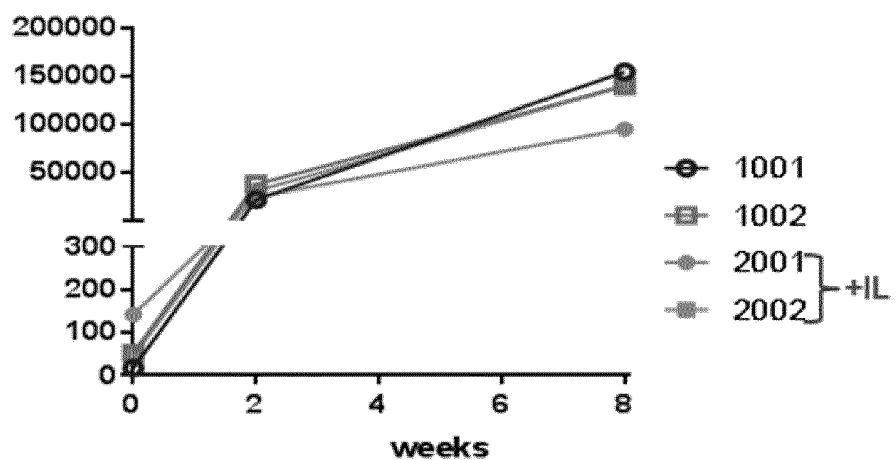
FIG. 5B shows the humoral immune response in control animals (1001, 1002) and intralipid pre-treated animals (2001, 2002), as measured by levels of anti-AAV neutralizing antibodies.

Humoral immune responses: To determine the potential effect of intralipid on the levels of antibodies generated against the AAV5 viral capsid proteins, assays for total and neutralizing antibodies were performed on monkey plasma samples obtained at baseline and over the course of the experiment (FIGS. 5A and 5B). After administration with AAV5-LP1-FIX in control animals (1001 and 1002) and intralipid pre-treated animals (2001 and 2002), the levels of anti-AAV total antibodies (FIG. 5A) and anti-AAV neutralizing antibodies (FIG. 5B) were measured. As shown in FIGS. 5A and 5B, anti-AAV total and neutralizing antibodies increased similarly for all the animals injected, regardless of pre-treatment with intralipid.

Figure 5C:
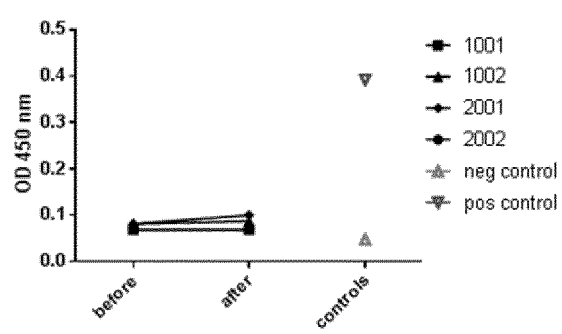
FIG. 5C shows the humoral immune response in control animals (1001, 1002) and intralipid pre-treated animals (2001, 2002), as measured by levels of total anti-hFIX antibodies.
Figure 5D:
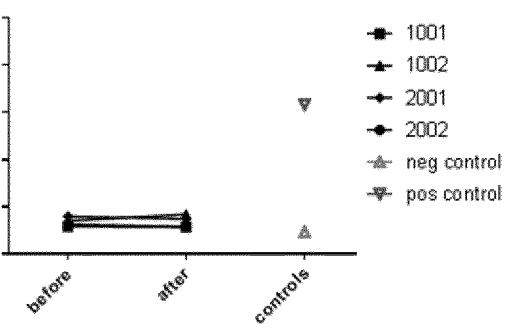
FIG. 5D shows the humoral immune response in control animals (1001, 1002) and intralipid pre-treated animals (2001, 2002), as measured by levels of total anti-hFIX antibodies.

The presence of anti-hFIX antibodies was also monitored in plasma samples obtained at baseline and at 56 days after administration of AAV5-LP1-FIX. Monkey serum deplete from IgG (cynomolgus serum) was used as a negative control. Monkey plasma samples known to be positive for the presence of anti-hFIX antibodies were used as positive control in the assay. No humoral immune response, as measured by levels of anti-hFIX total antibodies, could be detected against the transgene protein in control animals (1001 and 1002) or animals pre-treated with intralipid (2001 and 2002) (FIGS. 5C and 5D). The 1:25 and 1:50 referred to in the figures refers to the dilution factor used. The plasma samples were tested at 2 different dilutions with the same outcome.

Bio-distribution: The potential impact of Intralipid 20% pre-treatment on AAV off-targeting was assessed by detecting the presence of AAV vector DNA in the adrenal glands and spleen. The tissues were collected at time of sacrifice. Vector DNA levels were measured by QPCR.

Figure 6:
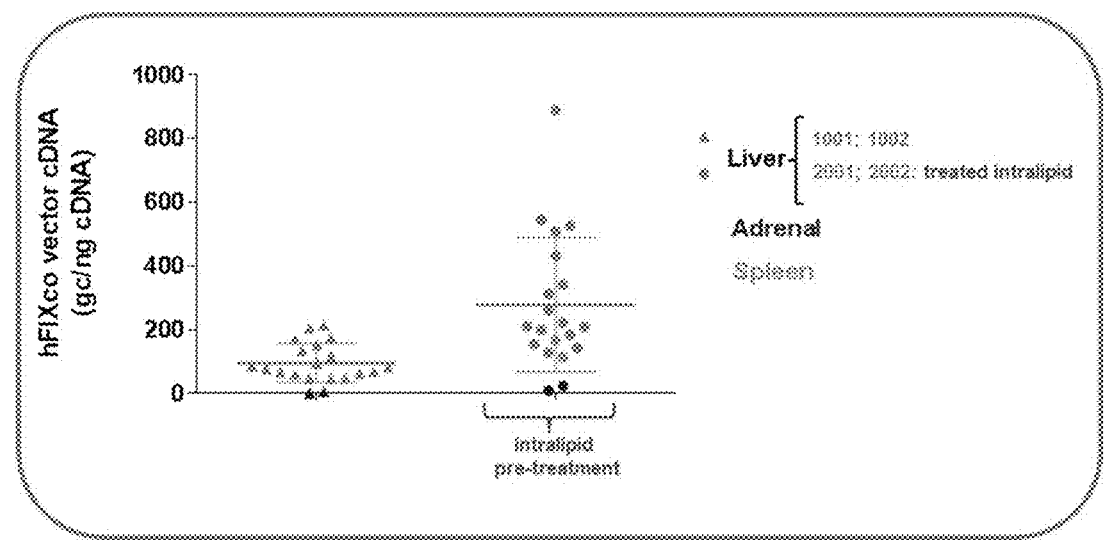
FIG. 6 shows the distribution of AAV5-LP1-hFIX vector DNA in liver lobes (8 per animal), spleen and adrenal tissues.

As shown in FIG. 6, pre-treatment with Intralipid 20% increased the AAV transduction not only in the liver, but also in the spleen, which is also part of the RES system. No apparent effect of Intralipid 20% on AAV transduction in the adrenal glands was observed.

Figure 7:
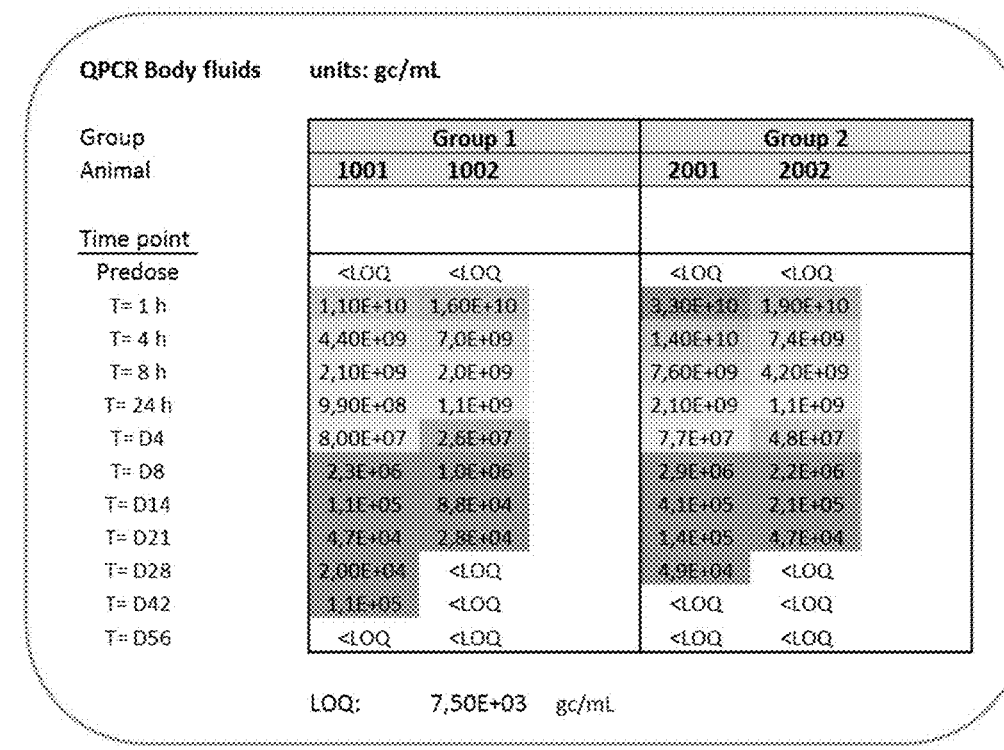
FIG. 7 shows a table of the levels of AAV vector DNA in plasma samples obtained from control animals and animals pre-treated with intralipid.

Shedding: The persistence of AAV vector DNA in blood was monitored over time by QPCR in plasma samples collected at pre-administration and 1, 4, 8, 24 hours and at 8, 14, 21, 28, 42 and 56 days after AAV administration. As shown in FIG. 7, levels of AAV vector DNA decreased over time and eventually returned to basal levels (e.g., limit of quantitation) between 28 and 56 days after AAV injection. During the first 8 hours after AAV injection, the levels of AAV vector DNA in the blood tended to be higher in animals pre-treated with intralipid (Group 2, 2001 and 2002) than in the control animals (Group 1, 1001 and 1002), which might account for the effect of intralipid on the blood clearance function from the RES organs (especially in liver).

Figure 8A:
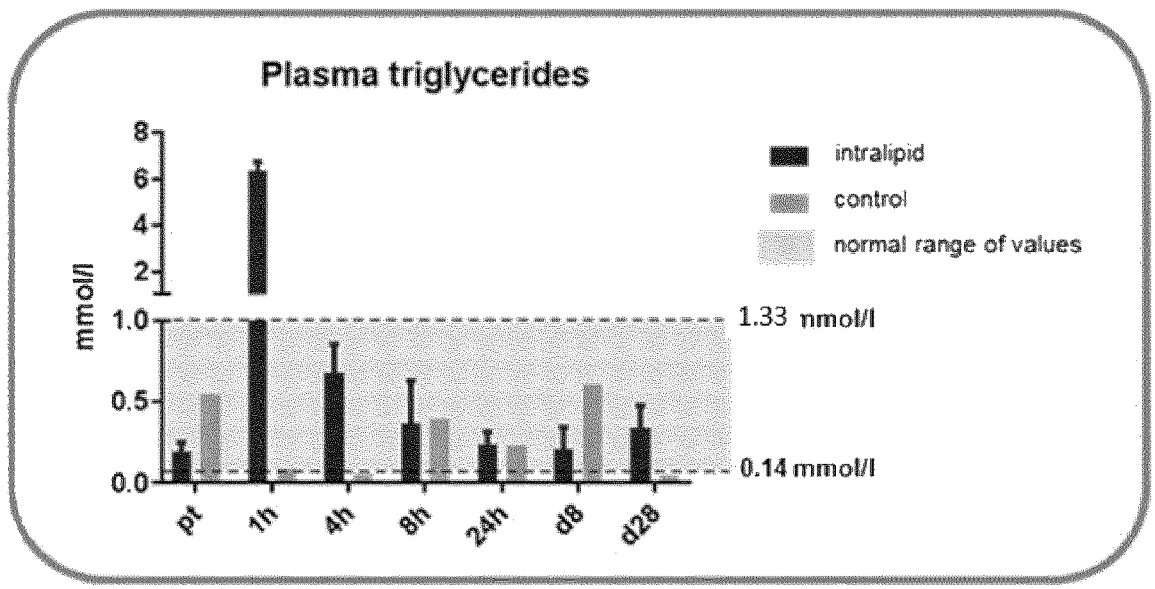
FIG. 8A shows lipid clearance in plasma samples obtained from a control animal, which were administered PBS, and an animal pre-treated with intralipid.
Figure 8B:
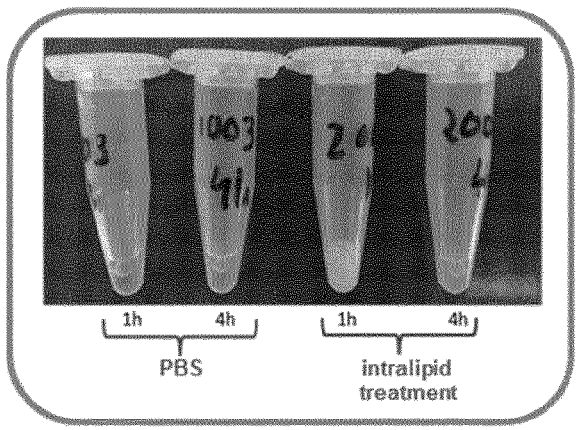
FIG. 8B shows sample tubes from the control animal and intralipid pre-treated animal.

Lipid clearance after intralipid treatment: The clearance of Intralipid in the blood was monitored over time in the animals injected intravenously with the Intralipid bolus. As a read-out, the triglycerides levels were measured in plasma samples obtained at pre-administration and 1, 4, 8, 24 hours and days 8 and 28 after AAV administration. As shown in FIG. 8A, the triglycerides returned to levels in the range of normal values (Xie L et al, 2013) within 5 hours after intralipid bolus injection.

Conclusions: Overall, the results obtained from this example showed that:
Following the treatment with Intralipid at a bolus dose of 2 g/kg before injection with AAV5-LP1-hFIX (9.7E12 gc/kg), AAV liver transduction was increased.
The AAV vector DNA levels in the liver tissue as well as the transgene protein expression levels in plasma were higher in the animals treated with Intralipid 20% as compared to control animals.
A better spreading and spatial distribution of AAV vector in the liver tissue was observed after Intralipid 20% pre-treatment. The diffusion of AAV vector DNA/hFIX mRNA in tissue increased with a spatial localization found around both portal and central veins.
AAV transduction was increased not only in the liver, but also in the spleen, which is part of the RES system.
No difference in humoral response to the AAV5 viral capsid protein was observed between the control animals and intralipid pre-treated animals. And, no humoral response was detected against the transgene protein in the control animals and intralipd pre-treated animals.
The clearance of Intralipid 20% in the blood occurred within 5 hours after intralipid bolus injection, which is compatible with a good safety profile.
During the first 8 hours after AAV injection, the levels of AAV vector DNA in the blood tended to be higher in animals pre-treated with intralipid compared to control animals, which might account for the effect of Intralipid on the blood clearance function from the RES organs (especially in liver).

Example 2—Analysis of AAV Gene Therapy Vector Dosage on Transduction Efficiency

In this example, the correlation between AAV gene therapy vector dose and transduction efficacy is investigated.

Experimental set-up: Non-human primates (NHPs, n=3) that tested negative for the presence of anti-AAV serotype 5 neutralizing antibodies are injected intravenously with a bolus of Intralipid 20% at the clinical dose (2 g/kg) one hour before administration of the AAV gene therapy vector (e.g., AAV5(160)-LP1-hFIX) at a dose of $5 \times 10^{12}$ gc/kg, $1 \times 10^{13}$ gc/kg, or $5 \times 10^{13}$ gc/kg (referred to as Groups 1, 2, and 3, respectively). Control groups (n=3) are injected with AAV5 (160)-LP1-hFIX at a dose of $5 \times 10^{12}$ gc/kg, $1 \times 10^{13}$ gc/kg or $5 \times 10^{13}$ gc/kg without prior treatment (referred to as Groups 4, 5, and 6, respectively). The animals are monitored for 8 weeks before sacrifice.

| Animals | Intralipid Bolus injection (day 0 of the exp.) | AAV5-LP1-hFIX injection (1 hour after Intralipid injection) |
| --- | --- | --- |
| Group 1 (3 animals) | Yes | $5 \times 10^{12}$ gc/kg |
| Group 2 (3 animals) | Yes | $1 \times 10^{13}$ gc/kg |
| Group 3 (3 animals) | Yes | $5 \times 10^{13}$ gc/kg |
| Group 4 (3 animals) | No | $5 \times 10^{12}$ gc/kg |
| Group 5 (3 animals) | No | $1 \times 10^{13}$ gc/kg |
| Group 6 (3 animals) | No | $5 \times 10^{13}$ gc/kg |

The negative controls are blood/plasma samples taken before any treatment and tissues from PBS animals (previous studies).

Analysis

Blood samples are taken on a weekly basis (and/or at the time points described below) and tissues are collected at time of sacrifice. The following parameters are monitored using the methods described in Example 1 or using standard methods known in the art:
Levels of circulating hFIX are measured by ELISA (time points: pre-treatment and days 4, 8, 14, 21, 28, 42 and 56)
Levels of Neutralizing/Total antibodies against AAV5 are measured by neutralizing antibody (NAB) assay and ELISA (time points: pre-treatment and days 4, 8, 14, 21, 28, 42 and 56)
Evaluation of the potential cellular immune responses induced against the AAV vector capsid after vector administration by purification peripheral blood lymphocytes, ELIspot (time points: pre-treatment and weeks, 1, 2, 4 and 8)
Bio-distribution in tissues at time of sacrifice, especially, in organs associated with the RES system such as the liver (8 liver lobes), spleen, lymphoid nodes (mesenteric, iliac, inguinal), kidneys, lungs, duodenum (Peyer's patches). Adrenal gland and heart, is investigated by detecting levels of AAV vector DNA and transgene mRNA by qPCR, FISH, IHC, and histology.

Shedding of AAV vector DNA in blood/plasma and urine are measured by qPCR (time points: pre-treatment and at 1, 4, 8 and 24 hours post-dose and at days 4, 8, 14, 21, 28, 42 and 56).

Clearance of intralipid in blood/plasma is determined by measuring triglycerides levels in blood/plasma (time points: pre-treatment and at 1, 4, 8 and 24 hours post-dose and at days 4, 8, 14, 21, 28, 42 and 56).

Haematology Parameters, such as red blood cell count, hemoglobin concentrations, hematocrit, mean corpuscular volume, red blood cell distribution width, mean corpuscular hemoglobin concentration, mean corpuscular hemoglobulin, reticulocyte percent, platelet count, white blood cell count, neutrophil count (absolute), lymphocyte count (absolute), monocyte count (absolute), eosinophil count (absolute), basophil count (absolute), and large unstained cells (absolute), are measured.

Clinical Chemistry Parameters, such as alanine aminotransferase, aspartate aminotransferase, alkaline phosphatase, gamma-glutamyltransferase, creatine kinase, total bilirubin (or indirect and direct bilirubin if total bilirubin is >17.1 µmol/L), urea, creatine, calcium, phosphate, total protein, albumin, globulin, albumin/globulin ratio, glucose, cholesterol, triglycerides, sodium, potassium, chloride, and sample quality, are measured.

Example 3—Analysis of Intralipid Dosage on AAV Gene Therapy Vector Transduction Efficiency In this example, the correlation between intralipid dose and AAV gene therapy vector transduction efficacy is investigated.

Experimental set-up: Non-human primates (NHPs, n=3) that tested negative for the presence of anti-AAV serotype 5 neutralizing antibodies are injected intravenously with a bolus of Intralipid 20% at the clinical dose of either 2 g/kg or 4 g/kg one hour before administration of AAV gene therapy vector (e.g., AAV5(160)-LP1-hFIX) at a dose of $1 \times 10^{13}$ gc/kg (referred to as Groups 1 and 2, respectively). A control group (n=3) is injected with AAV5(160)-LP1-hFIX at a dose of $1 \times 10^{13}$ gc/kg without prior intralipid treatment (referred to as Group 3). The animals are monitored for 8 weeks before sacrifice.

| Animals | Intralipid Bolus injection (day 0 of the exp.) | AAV5-LP1-hFIX injection (1 hour after Intralipid injection) |
|---|---|---|
| Group 1 (3 animals) | 2 g/kg | $1 \times 10^{13}$ |
| Group 2 (3 animals) | 4 g/kg | $1 \times 10^{13}$ |
| Group 3 (3 animals) | No | $1 \times 10^{13}$ |

The negative controls are blood/plasma samples taken before any treatment and tissues from PBS animals (previous studies).

Analysis

Blood samples are taken on a weekly basis (and/or at the time points described below) and tissues are collected at time of sacrifice. The following parameters are monitored using the methods described in Example 1 or using standard methods known in the art:

Levels of circulating hFIX are measured by ELISA (time points: pre-treatment and days 4, 8, 14, 21, 28, 42 and 56)

Levels of Neutralizing/Total antibodies against AAV5 are measured by neutralizing antibody (NAB) assay and ELISA (time points: pre-treatment and days 4, 8, 14, 21, 28, 42 and 56)

Evaluation of the potential cellular immune responses induced against the AAV vector capsid after vector administration by purification peripheral blood lymphocytes, ELIspot (time points: pre-treatment and weeks, 1, 2, 4 and 8)

Bio-distribution in tissues at time of sacrifice, especially, in organs associated with the RES system such as the liver (8 liver lobes), spleen, lymphoid nodes (mesenteric, iliac, inguinal), kidneys, lungs, duodenum (Peyer's patches). Adrenal gland and heart, is investigated by detecting levels of AAV vector DNA and transgene mRNA by qPCR, FISH, IHC, and histology.

Shedding of AAV vector DNA in blood/plasma and urine are measured by qPCR (time points: pre-treatment and at 1, 4, 8 and 24 hours post-dose and at days 4, 8, 14, 21, 28, 42 and 56).

Clearance of intralipid in blood/plasma is determined by measuring triglycerides levels in blood/plasma (time points: pre-treatment and at 1, 4, 8 and 24 hours post-dose and at days 4, 8, 14, 21, 28, 42 and 56).

Haematology Parameters, such as red blood cell count, hemoglobin concentrations, hematocrit, mean corpuscular volume, red blood cell distribution width, mean corpuscular hemoglobin concentration, mean corpuscular hemoglobulin, reticulocyte percent, platelet count, white blood cell count, neutrophil count (absolute), lymphocyte count (absolute), monocyte count (absolute), eosinophil count (absolute), basophil count (absolute), and large unstained cells (absolute), are measured.

Clinical Chemistry Parameters, such as alanine aminotransferase, aspartate aminotransferase, alkaline phosphatase, gamma-glutamyltransferase, creatine kinase, total bilirubin (or indirect and direct bilirubin if total bilirubin is >17.1 µmol/L), urea, creatine, calcium, phosphate, total protein, albumin, globulin, albumin/globulin ratio, glucose, cholesterol, triglycerides, sodium, potassium, chloride, and sample quality, are measured.

Clauses

1. A method of treating a disease in a human subject, comprising: administering to a human subject suffering from a disease a saturating agent and an adeno-associated virus (AAV) gene therapy vector, wherein the saturating agent is taken up by one or more cells of a reticuloendothelial system (RES).
2. The method of clause 1, wherein the one or more cells of a RES is selected from a Kupffer cell, sinusoidal endothelial cell (SEC), and hepatic stellate cell (HSC).
3. The method of clause 1, wherein the one or more cells of a RES is a Kupffer cell.
4. The method of clause 1, wherein the one or more cells of a RES is a sinusoidal endothelial cell (SEC).
5. The method of clause 1, wherein the one or more cells of a RES is a hepatic stellate cell (HSC).

6. The method of clause 1, wherein the one or more cells of a RES are two or more cells selected from a Kupffer cell, sinusoidal endothelial cell (SEC), and hepatic stellate cell (HSC).
7. The method of clause 6, wherein the two or more cells are a Kupffer cell and SEC.
8. The method of clause 6, wherein the two or more cells are a Kupffer cell and HSC.
9. The method of clause 6, wherein the two or more cells are a SEC and HSC.
10. The method of clause 1, wherein the one or more cells of a RES comprise a plurality of cells.
11. The method of clause 10, wherein at least 10%, 20%, 30%, 40%, 50%, 60%, 70%, 80%, 90%, 95% or more of the plurality of cells are Kupffer cells.
12. The method of clause 10, wherein at least 10%, 20%, 30%, 40%, 50%, 60%, 70%, 80%, 90%, 95% or more of the plurality of cells are sinusoidal endothelial cells (SECs).
13. The method of clause 10, wherein at least 10%, 20%, 30%, 40%, 50%, 60%, 70%, 80%, 90%, 95% or more of the plurality of cells are hepatic stellate cells (HSCs).
14. The method of clause 1, wherein the saturating agent comprises one or more nutrients selected from carbohydrates, amino acids, lipids, vitamins, dietary minerals, or any combination thereof.
15. The method of clause 1, wherein the saturating agent comprises one or more lipids selected from triglycerides, steroids, phospholipids, or any combination thereof
16. The method of clause 15, wherein the phospholipids are selected from phosphatidylethanolamine, phosphatidylcholine, phosphatidylinositol, phosphatidylserine, lecithin, plasmalogen, and sphingomyelin.
17. The method of clause 1, wherein the saturating agent comprises a phospholipid.
18. The method of clause 17, wherein the phospholipid is phosphatidylcholine.
19. The method of clause 18, wherein the phosphatidylcholine is selected from palmitoyl-oleyl-sn-phosphatidylcholine, 1-Oleoyl-2-palmitoyl-phosphatidylcholine, and L-α-phosphatidylcholine.
20. The method of clause 18, wherein the phosphatidylcholine is not L-α-phosphatidylcholine.
21. The method of clause 1, wherein the saturating agent comprises a nutritional supplement selected from a total parenteral nutritional (TPN) supplement, peripheral parenteral nutrition (PPN) supplement, Aminosyn®, AMINOSYN®-HBC, AMINOSYN®-HF, AMINOSYN®-RF, BRANCHAMIN®, FREAMINE HBC®, FREAMINE® III, HEPATAMINE®, KABIVEN®, PERIKABIVEN®, NOVAMINE®, Premasol, PROCALAMINE®, ProSol, RENAMIN®, TROPHAMINE®, or any combination thereof
22. The method of clause 1, wherein the saturating agent comprises an emulsion.
23. The method of clause 22, wherein the emulsion comprises soybean oil, vegetable oil, fish oil, phospholipids, and glycerol, or any combination thereof
24. The method of clause 22, wherein the emulsion comprises droplets having a size larger than 0.1 µm.
25. The method of clause 22, wherein the emulsion comprises droplets having a size smaller than 2 µm.
26. The method of clause 22, wherein the emulsion comprises droplets having a size between 0.1 µm and 2 µm.
27. The method of clause 22, wherein the emulsion comprises a lipid emulsion.
28. The method of clause 22, wherein the emulsion comprises a fat emulsion.
29. The method of clause 28, wherein the fat emulsion is selected from of INTRALIPID® 10%, INTRALIPID® 20%, and INTRALIPID® 30%.
30. The method of clause 282, wherein the lipid emulsion is Clinolipid.
31. The method of clause 28, wherein the fat emulsion is selected from LIPOSYN®, LIPOSYN® II, and LIPOSYN® III.
32. The method of clause 1, wherein the saturating agent comprises a nanoparticle.
33. The method of clause 1, wherein the saturating agent is a microsphere.
34. The method of clause 1, wherein the saturating agent is selected from a micelle, reverse micelle, and liposome.
35. The method of clause 34, wherein the liposome is an L-α-phosphatidylcholine liposome.
36. The method of clause 34, wherein the liposome is selected from a multilamellar vesicle (MLV), unilamellar vesicle, and cochleate vesicle.
37. The method of clause 36, wherein the unilamellar vesicle is selected from a small unilamellar vesicle (SUV) and a large unilamellar vesicle (LUV).
38. The method of clause 32, wherein the nanoparticle is a lipid nanoparticle.
39. The method of clause 32, wherein the nanoparticle is a dispersed phase in an emulsion or an internal phase in a suspension.
40. The method of clause 32, wherein the nanoparticle is selected from a micellar solution and solid lipid nanoparticle (SLN).
41. The method of clause 32, wherein the nanoparticle has a diameter of between 0.2 to 300 nm.
42. The method of clause 1, wherein the saturating agent comprises an empty viral capsid.
43. The method of clause 1, wherein the saturating agent is not an empty viral capsid.
44. The method of clause 42 or 43, wherein the empty viral capsid is an adeno-associated virus capsid.
45. The method of clause 1, further comprising one or more additional saturating agents.
46. The method of clause 45, wherein the saturating agent of clause 1 is different from the one or more additional saturating agents of clause 45.
47. The method of clause 1, wherein the AAV is selected from the group consisting of AAV serotype 1 (AAV1), AAV2, AAV3, AAV4, AAV5, AAV6, AAV7, AAV8, AAV9, AAV10, and AAV11.
48. The method of clause 1, wherein the AAV is AAV1 or AAV5.
49. The method of clause 1, wherein the AAV is AAV6, AAV7, AAV8, AAV9, or AAV10.
50. The method of clause 1, wherein the AAV was discovered in human cells.
51. The method of clause 1, wherein the AAV was discovered in non-human primate cells.
52. The method of clause 51, wherein the non-human primate cells are selected from rhesus cells and cynomolgus cells.
53. The method of clause 1, wherein the AAV is a recombinant AAV (rAAV).

54. The method of clause 53, wherein the rAAV is rAAV2/5, wherein the rAAV2/5 comprises at least a portion of AAV2 and AAV5.
55. The method of clause 1, wherein the AAV is a chimeric AAV (AAV$^{ch}$).
56. The method of clause 55, wherein the AAV$^{ch}$ is a chimeric AAV serotype 5 (AAV5$^{ch}$).
57. The method of clause 1, wherein the AAV gene therapy vector encodes a therapeutic gene or fragment thereof
58. The method of clause 57, wherein the therapeutic gene encodes factor IX (FIX), factor VIII (FVIII), alpha-galactosidase, or alpha-N-acetylgalactosaminidase, or modified forms thereof.
59. The method of clause 57, wherein the therapeutic gene encodes alpha-1 antitrypsin (AAT), aromatic amino acid decarboxylase (AADC), ATPase Sarcoplasmic/Endoplasmic Reticulum Ca2+ Transporting 2 (ATP2A2), cystic fibrosis transmembrane conductance regulator (CTFR), glutamic acid decarboxylase 65 kDa protein (GAD65), glutamic acid decarboxylase 67 kDa protein (GAD67), lipoprotein lipase (LPL), nerve growth factor (NGF), neurturin (NTN), porphobilinogen deaminase (PBGD), sarcoglycan alpha (SGCA), soluble fms-like tyrosine kinase-1 (sFLT-1), S100 calcium binding protein A1 (S100A1), survival of motor neuron 1 (SMN1), tripeptidyl peptidase I (TPP1), tumor necrosis factor receptor (TNFR)-immunoglobulin (IgG1) Fc fusion (TNFR:Fc), interferon beta (IFN-(3), neuropeptide Y receptor Y2, alpha glucosidase, C9orf72, superoxide dismutase (SOD), CFTR, chondroitinase, HexA, or HexB.
60. The method of clause 1, wherein the AAV gene therapy vector comprises a polynucleotide encoding a small interfering RNA (siRNA), a miRNA, or a shRNA that targets a gene of interest.
61. The method of clause 60, wherein the gene of interest is a Htt gene.
62. The method of clause 57, wherein the therapeutic gene encodes a factor IX (FIX) protein.
63. The method of clause 57, wherein the therapeutic gene encodes a human protein.
64. The method of clause 1, wherein the AAV gene therapy vector comprises a polynucleotide encodes a microRNA (miRNA).
65. The method of clause 64, wherein the miRNA silences a gene of interest.
66. The method of clause 1, further comprising one or more therapeutic agents.
67. The method of clause 66, wherein the therapeutic agent is selected from a virus-based therapy, non-virus-based therapy, and gene therapy.
68. The method of clause 66, wherein the therapeutic agent comprises a virus-based therapy.
69. The method of clause 66, wherein the therapeutic agent comprises a virus-based therapy selected from a lentivirus, retrovirus, and adenovirus-based therapy.
70. The method of clause 66, wherein the therapeutic agent comprises an additional AAV gene therapy vector.
71. The method of clause 70, wherein the AAV gene therapy vector and the additional AAV gene therapy comprise AAVs of different serotypes.
72. The method of clause 70, wherein the AAV gene therapy vector and the additional AAV gene therapy comprise AAVs of the same serotype.
73. The method of clause 1, wherein the saturating agent and the AAV gene therapy vector are administered sequentially.
74. The method of clause 1, wherein the saturating agent and the AAV gene therapy vector are administered concurrently.
75. The method of clause 1, wherein the saturating agent is administered prior to administration of the AAV gene therapy vector.
76. The method of clause 1, wherein the saturating agent is administered at least 5, 10, 15, 20, 25, 30, 35, 40, 45, 50, 55, 60, 65, 70, 75, 80, 85, or 90 or more minutes prior to administration of the AAV gene therapy vector.
77. The method of clause 1, wherein the saturating agent is administered between 0.5 to 24 hours, between 0.5 to 12 hours, or between 1 to 5 hours prior to administration of the AAV gene therapy vector.
78. The method of clause 45, wherein the saturating agent and the one or more additional saturating agents are administered concurrently.
79. The method of clause 45, wherein the saturating agent and the one or more additional saturating agents are administered sequentially.
80. The method of clause 45, wherein the saturating agent is administered prior to administration of the one or more additional saturating agents.
81. The method of clause 45, wherein the saturating agent is administered at least 5, 10, 15, 20, 25, 30, 35, 40, 45, 50, 55, 60, 65, 70, 75, 80, 85, 90, 95, 100, 110, 120, 130, 140, or 150 or more minutes prior to administration of the one or more additional saturating agents.
82. The method of clause 45, wherein the saturating agent is administered at least 1, 2, 3, 4, 5, 6, 7, 8, 9, 10, 11, 12, 13, 14, 15, 16, 17, 18, 19, 20, 21, 22, 23, or 24 or more hours prior to administration of the one or more additional saturating agents.
83. The method of clause 1, wherein the saturating agent is administered for at least 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 130, 140, or 150 or more minutes.
84. The method of clause 1, wherein the AAV gene therapy vector is administered for at least 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 130, 140, or 150 or more minutes.
85. The method of clause 66, wherein the AAV gene therapy vector and the one or more therapeutic agents are administered concurrently.
86. The method of clause 66, wherein the AAV gene therapy vector and the one or more therapeutic agents are administered sequentially.
87. The method of clause 66, wherein the AAV gene therapy vector is administered prior to administration of the one or more therapeutic agents.
88. The method of clause 66, wherein the AAV gene therapy vector is administered at least 5, 10, 15, 20, 25, 30, 35, 40, 45, 50, 55, 60, 65, 70, 75, 80, 85, 90, 95, 100, 110, 120, 130, 140, or 150 or more minutes prior to administration of the one or more therapeutic agents.
89. The method of clause 66, wherein the AAV gene therapy vector is administered at least 1, 2, 3, 4, 5, 6, 7, 8, 9, 10, 11, 12, 13, 14, 15, 16, 17, 18, 19, 20, 21, 22, 23, or 24 or more hours prior to administration of the one or more therapeutic agents.
90. The method of clause 45, wherein the one or more additional saturating agents is administered for at least 1, 2, 3, 4, 5, 10, 15, 20, 25, 30, 35, 40, 45, 50, 55, 60, 65, 70, 75, 80, 85, 90, 95, 100, 110, 120, 130, 140, or 150 or more minutes.
91. The method of clause 66, wherein the one or more therapeutic agents is administered for at least 1, 2, 3, 4, 5, 10, 15, 20, 25, 30, 35, 40, 45, 50, 55, 60, 65, 70, 75, 80, 85, 90, 95, 100, 110, 120, 130, 140, or 150 or more minutes.
92. The method of clause 1, wherein the saturating agent is administered systemically.
93. The method of clause 92, wherein the systemic administration comprises enteral administration.
94. The method of clause 93, wherein enteral administration is selected from oral, sublingual, and rectal administration.
95. The method of clause 92, wherein the systemic administration comprises parenteral administration.
96. The method of clause 95, wherein parenteral administration is selected from inhalation, injection, and transdermal administration.
97. The method of clause 96, wherein administration by injection is selected from intravenous, intramuscular, subcutaneous, intra-arterial, intra-articular, intrathecal, and intradermal.
98. The method of clause 1, wherein the AAV gene therapy vector is administered systemically.
99. The method of clause 98, wherein the systemic administration comprises parenteral administration.
100. The method of clause 99, wherein parenteral administration comprises an injection.
101. The method of clause 100, wherein administration by injection is selected from intravenous, intramuscular, subcutaneous, intra-arterial, intra-articular, intrathecal, and intradermal.
102. The method of clause 1, wherein the saturating agent and/or AAV gene therapy vector is administered locally.
103. The method of clause 102, wherein local administration comprises administering the saturating agent and/or AAV gene therapy vector at or near a target organ.
104. The method of clause 103, wherein administration comprises an intravenous, intramuscular, subcutaneous, intra-arterial, intra-articular, intrathecal, or intradermal injection.
105. The method of clause 103, wherein the target organ is liver, lung, spleen, lymph nodes, kidney, small intestine, or brain.
106. The method of clause 1, wherein the route of administration for the saturating agent is different from the route of administration for the AAV gene therapy vector.
107. The method of clause 1, wherein the route of administration for the saturating agent is the same as the route of administration for the AAV gene therapy vector.
108. The method of clause 45, wherein the route of administration for the saturating agent of clause 1 is different from the route of administration for the one or more additional saturating agents of clause 45.
109. The method of clause 45, wherein the route of administration for the saturating agent of clause 1 is the same as the route of administration for the one or more additional saturating agents of clause 45.
110. The method of clause 66, wherein the route of administration for the AAV gene therapy vector is different from the route of administration for the one or more therapeutic agents.
111. The method of clause 66, wherein the route of administration for the AAV gene therapy vector is different from the route of administration for the one or more therapeutic agents.
112. The method of clause 1, wherein administering the saturating agent and/or therapeutic agent comprises delivering the saturating agent and/or therapeutic agent to an organ.
113. The method of clause 112, wherein the organ is from an organ system selected from a musculoskeletal system, digestive system, respiratory system, urinary system, reproductive system, endocrine system, circulatory system, nervous system, and integumentary system.
114. The method of clause 112, wherein the organ is selected from a brain, eye, thyroid, lung, heart, pancreas, liver, spleen, bladder, stomach, kidney, small intestine, lymph node, and prostate.
115. The method of clause 112, wherein the organ is a liver.
116. The method of clause 115, wherein the saturating agent and the AAV gene therapy vector are delivered to one or more cells of the liver.
117. The method of clause 116, wherein the saturating agent is primarily taken up by the one or more cells of a RES.
118. The method of clause 116, wherein at least 40%, 45%, 50%, 55%, 60%, 65%, 70%, 75%, 80%, 85%, 90%, or 95% or more of the saturating agent is taken up by the one or more cells of a RES.
119. The method of clause 116, wherein less than 10%, 20%, 30%, 40%, 50%, 55%, 60%, 65%, 70%, 75%, 80%, 85%, 90%, or 95% of the saturating agent is taken up by parenchymal liver cells.
120. The method of clause 116, wherein less than 10%, 20%, 30%, 40%, 50%, 55%, 60%, 65%, 70%, 75%, 80%, 85%, 90%, or 95% of the AAV gene therapy vector is taken up by the one or more cells of a RES.
121. The method of clause 116, wherein at least 20%, 25%, 30%, 35%, 40%, 45%, 50%, 55%, 60%, 65%, 70%, 75%, 80%, 85%, 90%, or 95% or more of the AAV gene therapy vector is taken up by parenchymal liver cells.
122. The method of clause 116, wherein the cells of the liver that primarily take up the saturating agent are different from the cells of the liver that primarily take up the AAV gene therapy vector.
123. The method of clause 116, wherein the saturating agent is primarily taken up by non-parenchymal liver cells and the AAV gene therapy vector is primarily taken up by parenchymal liver cells.
124. The method of clause 115, wherein the AAV gene therapy vector transduces at least 10%, 20%, 30%, 40%, 50%, 55%, 60%, 65%, 70%, 75%, 80%, 85%, 90%, or 95% or more of parenchymal liver cells.
125. The method of clause 1, wherein the dosage of the saturating agent is 0.5 g/kg, 1 g/kg, 1.5 g/kg, 2 g/kg, 2.5 g/kg, 3 g/kg, 3.5 g/kg, 4 g/kg, 4.5 g/kg, 5 g/kg, 5.5 g/kg, 6 g/kg, 6.5 g/kg, 7 g/kg, 7.5 g/kg, 8 g/kg, 8.5 g/kg, 9 g/kg, 9.5 g/kg, or 10 g/kg or more.

126. The method of clause 1, wherein the dosage of the saturating agent is less than 5 g/kg, 5.5 g/kg, 6 g/kg, 6.5 g/kg, 7 g/kg, 7.5 g/kg, 8 g/kg, 8.5 g/kg, 9 g/kg, 9.5 g/kg, or 10 g/kg.
127. The method of clause 1, wherein the dosage of the saturating agent is between 0.5 g/kg and 5 g/kg.
128. The method of clause 1, wherein the dosage of the saturating agent is 2 g/kg.
129. The method of clause 1, wherein the dosage of the saturating agent is 4 g/kg.
130. The method of clause 45, wherein the dosage of the saturating agent of clause 1 is different from the dosage of the one or more additional saturating agents of clause 45.
131. The method of clause 1, wherein the dosage of the AAV gene therapy vector is $1\times10^{10}$ gc/kg, $5\times10^{10}$ gc/kg, $1\times10^{11}$ gc/kg, $5\times10^{11}$ gc/kg, $1\times10^{12}$ gc/kg, $2\times10^{12}$ gc/kg, $3\times10^{12}$ gc/kg, $4\times10^{12}$ gc/kg, $5\times10^{12}$ gc/kg, $6\times10^{12}$ gc/kg, $7\times10^{12}$ gc/kg, $8\times10^{12}$ gc/kg, $9\times10^{12}$ gc/kg, $1\times10^{13}$ gc/kg, $5\times10^{13}$ gc/kg, $1\times10^{14}$ gc/kg, $5\times10^{14}$ gc/kg, or $1\times10^{15}$ gc/kg or more.
132. The method of clause 1, wherein the dosage of the AAV gene therapy vector is less than $1\times10^{13}$ gc/kg, $5\times10^{13}$ gc/kg, $1\times10^{14}$ gc/kg, $5\times10^{14}$ gc/kg, or $1\times10^{15}$ gc/kg.
133. The method of clause 1, wherein the dosage of the AAV gene therapy vector is between $1\times10^{12}$ gc/kg and $1\times10^{14}$ gc/kg.
134. The method of clause 1, wherein the dosage of the AAV gene therapy vector is between $5\times10^{12}$ gc/kg and $5\times10^{13}$ gc/kg.
135. The method of clause 1, wherein the dosage of the AAV gene therapy vector is $4\times10^{12}$ gc/kg, $4.5\times10^{12}$ gc/kg, $5\times10^{12}$ gc/kg, $5.5\times10^{12}$ gc/kg, $6\times10^{12}$ gc/kg, $6.5\times10^{12}$ gc/kg, $7\times10^{12}$ gc/kg, $7.5\times10^{12}$ gc/kg, $8\times10^{12}$ gc/kg, $8.5\times10^{12}$ gc/kg, $8.6\times10^{12}$ gc/kg, $8.7\times10^{12}$ gc/kg, $8.8\times10^{12}$ gc/kg, $8.9\times10^{12}$ gc/kg, $9\times10^{12}$ gc/kg, $9.1\times10^{12}$ gc/kg, $9.2\times10^{12}$ gc/kg, $9.3\times10^{12}$ gc/kg, $9.4\times10^{12}$ gc/kg, $9.5\times10^{12}$ gc/kg, $9.6\times10^{12}$ gc/kg, $9.7\times10^{12}$ gc/kg, $9.8\times10^{12}$ gc/kg, $9.9\times10^{12}$ gc/kg, $1\times10^{13}$ gc/kg, $1.5\times10^{13}$ gc/kg, $2\times10^{11}$ gc/kg, $2.5\times10^{13}$ gc/kg, $3\times10^{11}$ gc/kg, $3.5\times10^{13}$ gc/kg, $4\times10^{13}$ gc/kg, $4.5\times10^{13}$ gc/kg, $5\times10^{13}$ gc/kg, $5.5\times10^{13}$ gc/kg, or $6\times10^{11}$ gc/kg or more.
136. The method of clause 1, wherein the dosage of the AAV gene therapy vector is $9.7\times10^{12}$ gc/kg.
137. The method of clause 1, wherein the dosage of the AAV gene therapy vector is $5\times10^{13}$ gc/kg.
138. The method of clause 1, wherein the dosage of the AAV gene therapy vector is inversely proportional to the dosage of the saturating agent.
139. The method of clause 1, wherein the disease is a genetic disorder.
140. The method of clause 139, wherein the genetic disorder comprises a mutation in a gene.
141. The method of clause 139, wherein the genetic disorder is a metabolic disorder.
142. The method of clause 1, wherein the disease is selected from acute intermittent *Porphyria* (AIP), age-related macular degeneration, Alzheimer's disease, arthritis, Batten disease, Canavan disease, Citrullinemia type 1, Crigler Najjar, congestive heart failure, cystic fibrosis, Duchene muscular dystrophy, dyslipidemia, glycogen storage disease type I (GSD-I), hemophilia A, hemophilia B, hereditary emphysema, homozygous familial hypercholesterolemia (HoFH), Huntington's disease (HD), Leber's congenital amaurosis, methylmalonic academia, ornithine transcarbamylase deficiency (OTC), Parkinson's disease, phenylketonuria (PKU), spinal muscular atrophy, paralysis, Wilson disease, epilepsy, Pompe disease, amyotrophic lateral sclerosis (ALS), Tay-Sachs disease, hyperoxaluria (PH-1), spinocerebellar ataxia type 1 (SCA-1), SCA-3, u-dystrophin, Gaucher's types II or III, arrhythmogenic right ventricular cardiomyopathy (ARVC), Fabry disease, familial Mediterranean fever (FMF), proprionic acidemia, fragile X syndrome, Rett sundrome, Niemann-Pick, and Krabbe disease.
143. The method of clause 1, wherein the disease is selected from hemophilia A, hemophilia B, Huntington's disease (HD).
144. A method of treating a disease, comprising: administering a saturating agent and a gene therapy vector to a subject suffering from the disease, wherein the saturating agent is taken up by one or more cells of a reticuloendothelial system (RES), wherein the gene therapy vector does not comprise an adenovirus-based therapy, and wherein the disease is not cancer.
145. A method of treating a disease, comprising: administering a saturating agent and a therapeutic agent to a subject suffering from the disease, wherein the saturating agent is taken up by one or more cells of a reticuloendothelial system (RES), wherein the therapeutic agent comprises an adeno-associated virus gene therapy vector, and wherein disease is not cancer.
146. A method of treating a disease, comprising: administering a saturating agent and an adeno-associated virus gene therapy vector to a subject suffering from the disease, wherein the saturating agent is taken up by one or more cells of a reticuloendothelial system (RES).
147. A method of treating hemophilia, comprising: administering a saturating agent and an adeno-associated virus gene therapy vector to a subject suffering from hemophilia, wherein the saturating agent is taken up by one or more cells of a reticuloendothelial system (RES).
148. A method of treating Huntington's disease, comprising: administering a saturating agent and an adeno-associated virus gene therapy vector to a subject suffering from Huntington's disease, wherein the saturating agent is taken up by one or more cells of a reticuloendothelial system (RES).
149. A method of treating a cardiovascular disease, comprising: administering a saturating agent and an adeno-associated virus gene therapy vector to a subject suffering from the cardiovascular disease, wherein the saturating agent is taken up by one or more cells of a reticuloendothelial system (RES).
150. A method of increasing expression of a gene in a liver, comprising: administering a saturating agent and an adeno-associated virus gene therapy vector to a subject, wherein the subject is a human, wherein the saturating agent is taken up by one or more cells of a reticuloendothelial system (RES).
151. A method of increasing expression of a gene in parenchymal liver cells, comprising administering a saturating agent and an adeno-associated virus gene therapy vector to a subject, wherein the subject is a human, wherein the saturating agent is taken up by one or more cells of a reticuloendothelial system (RES).
152. A kit comprising a saturating agent and an adeno-associated virus gene therapy vector, wherein the saturating agent is taken up by one or more cells of a reticuloendothelial system (RES).

The invention claimed is:

1. A method of treating a human subject, comprising administering an adeno-associated virus (AAV) gene therapy vector to a human subject having been administered a saturating agent comprising soybean oil, egg yolk phospholipids, glycerine, and water, wherein the saturating agent is taken up by the reticuloendothelial system (RES), wherein transduction efficiency of the AAV gene therapy vector is increased at least 3 fold for 35 days post administration compared to the transduction efficiency in the absence of the saturating agent.

2. The method according to claim 1, wherein the saturating agent is selected from the group consisting of:
   (a) a saturating agent comprising 10% soybean oil, 1.2% egg yolk phospholipids, 2.25% glycerin, and water;
   (b) a saturating agent comprising 20% soybean oil, 1.2% egg yolk phospholipids, 2.25% glycerin, and water; and
   (c) a saturating agent comprising 30% soybean oil, 1.2% egg yolk phospholipids, 2.25% glycerin, and water.

3. The method according to claim 1, wherein the saturating agent comprises triglycerides, and wherein the plasma concentration of triglycerides in the blood of the human subject is at least 3 mmol/L prior to administration of the AAV gene therapy vector.

4. The method according to claim 1, wherein the saturating agent has been administered to the human subject at least 15 minutes or more prior to administration of the AAV gene therapy vector.

5. The method according to claim 1, wherein the AAV gene therapy vector is administered via the bloodstream.

6. The method according to claim 1, wherein the treatment is of the liver of the human subject.

7. The method according to claim 1, for the treatment of a disease selected from the group consisting of acute intermittent *Porphyria* (AIP), age-related macular degeneration, Alzheimer's disease, arthritis, Batten disease, Canavan disease, Citrullinemia type 1, Crigler Najjar, congestive heart failure, cystic fibrosis, Duchene muscular dystrophy, dyslipidemia, glycogen storage disease type I (GSD-I), hemophilia A, hemophilia B, hereditary emphysema, homozygous familial hypercholesterolemia (HoFH), Huntington's disease (HD), Leber's congenital amaurosis, methylmalonic academia, ornithine transcarbamylase deficiency (OTC), Parkinson's disease, phenylketonuria (PKU), spinal muscular atrophy, paralysis, Wilson disease, epilepsy, Pompe disease, amyotrophic lateral sclerosis (ALS), Tay-Sachs disease, hyperoxaluria (PH-1), spinocerebellar ataxia type 1 (SCA-1), SCA-3, u-dystrophin, Gaucher's types II or III, arrhythmogenic right ventricular cardiomyopathy (ARVC), Fabry disease, familial Mediterranean fever (FMF), proprionic acidemia, fragile X syndrome, Rett syndrome, Niemann-Pick, Krabbe disease, hemophilia A, hemophilia B, Huntington's disease (HD) and cardiac disease.

8. The method according to claim 7, for the treatment of a disease selected from haemophilia A, haemophilia B, and Huntington's disease (HD).

* * * * *